(12) United States Patent
Sun et al.

(10) Patent No.: US 12,167,852 B2
(45) Date of Patent: *Dec. 17, 2024

(54) SURGICAL STAPLING DEVICE WITH POWERED HANDLE ASSEMBLY

(71) Applicant: Covidien LP, Mansfield, MA (US)

(72) Inventors: Xiaowen Sun, Shanghai (CN); Yezhou Wu, Shanghai (CN); Lin Chen, Shanghai (CN); Fen Du, Shanghai (CN); Shouwei Li, Shanghai (CN)

(73) Assignee: Covidien LP, Mansfield, MA (US)

( * ) Notice: Subject to any disclaimer, the term of this patent is extended or adjusted under 35 U.S.C. 154(b) by 25 days.

This patent is subject to a terminal disclaimer.

(21) Appl. No.: 18/105,076

(22) Filed: Feb. 2, 2023

(65) Prior Publication Data
US 2023/0181189 A1    Jun. 15, 2023

Related U.S. Application Data

(63) Continuation of application No. 17/279,836, filed as application No. PCT/CN2018/110427 on Oct. 16, 2018, now Pat. No. 11,571,214.

(51) Int. Cl.
*A61B 17/072*    (2006.01)
*A61B 17/00*    (2006.01)
*A61B 17/29*    (2006.01)

(52) U.S. Cl.
CPC .......... *A61B 17/07207* (2013.01); *A61B 2017/00398* (2013.01); *A61B 2017/07257* (2013.01); *A61B 2017/07271* (2013.01); *A61B 2017/2923* (2013.01)

(58) Field of Classification Search
CPC ........ A61B 17/068; A61B 2017/07207; A61B 2017/07257; A61B 2017/07271
See application file for complete search history.

(56) References Cited

U.S. PATENT DOCUMENTS

| | | | |
|---|---|---|---|
| 7,959,050 B2* | 6/2011 | Smith | A61B 17/115 227/176.1 |
| 11,571,214 B2* | 2/2023 | Sun | A61B 17/07207 |
| 2008/0245842 A1 | 10/2008 | Marczyk | |

(Continued)

FOREIGN PATENT DOCUMENTS

| CN | 202776434 U | 3/2013 |
|---|---|---|
| EP | 3009094 A1 | 4/2016 |

OTHER PUBLICATIONS

Supplementary European Search Report dated May 16, 2022, issued in corresponding EP Appln. No. 18937500, 10 pages.

(Continued)

*Primary Examiner* — Michelle Lopez

(57) ABSTRACT

A surgical stapling device includes a staple reload and a handle assembly that supports a drive rack, a motor assembly, a gear assembly, a reload select mechanism, and a safety toggle mechanism. The gear assembly is adapted to facilitate uncoupling of the motor assembly from the drive rack to allow manual movement of the drive rack. The reload select mechanism allows the length of a stroke of the drive rack to be selectively adjusted to allow the stapling device to accommodate different length staple reloads. The safety toggle mechanism is provided to move the stapling device from a non-firing state to a firing state to allow for firing of the stapling device.

20 Claims, 16 Drawing Sheets

(56) References Cited

U.S. PATENT DOCUMENTS

2009/0057369 A1     3/2009   Smith et al.
2016/0374684 A1   12/2016   DiNardo et al.
2017/0290583 A1   10/2017   Reed et al.

OTHER PUBLICATIONS

International Search Report dated May 29, 2019, issued in corresponding international appln. No. PCT/CN2018/110427, 9 pages.

* cited by examiner

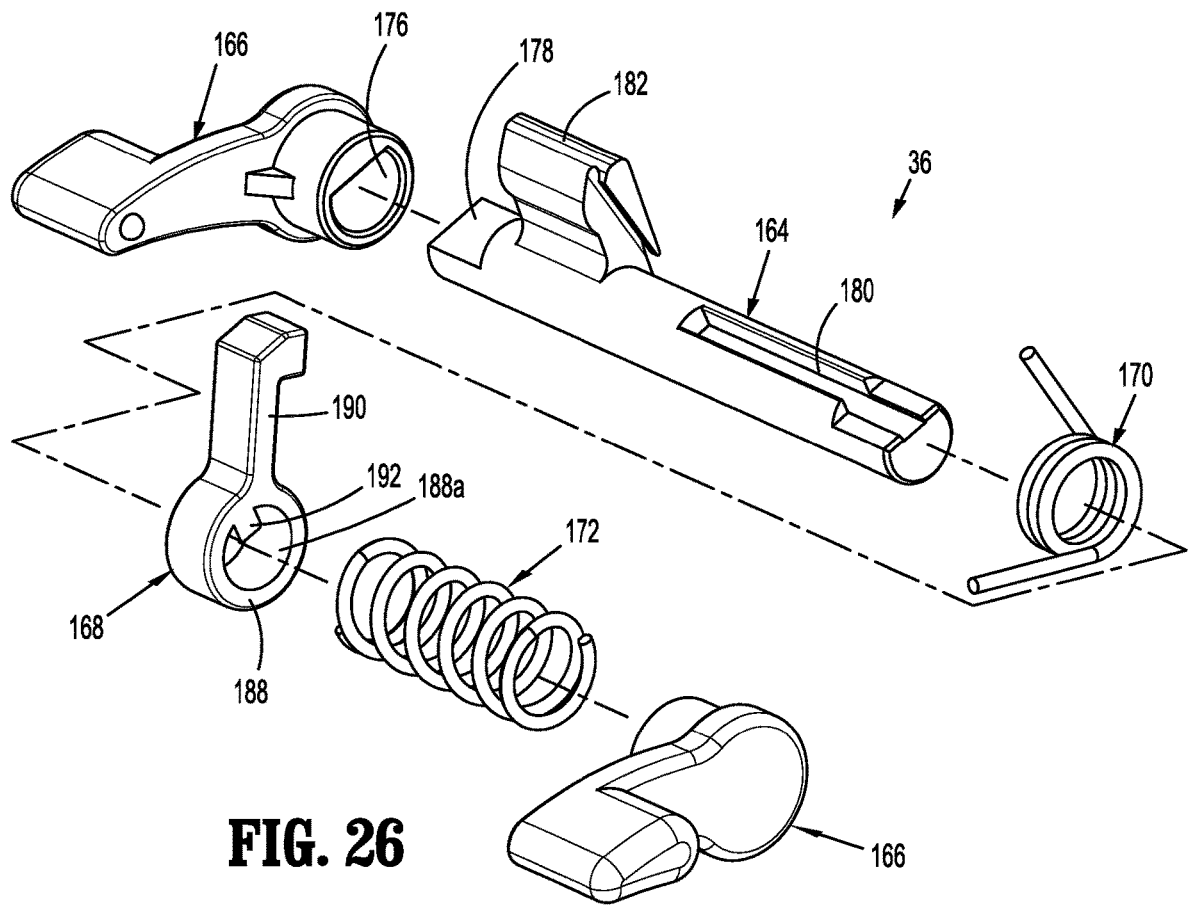
FIG. 26
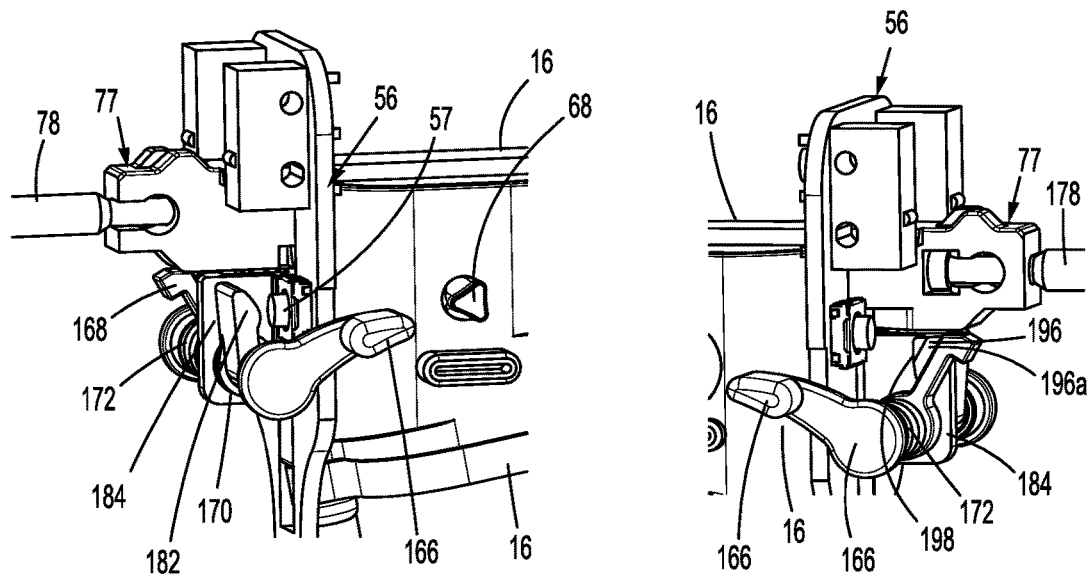
FIG. 27  FIG. 28

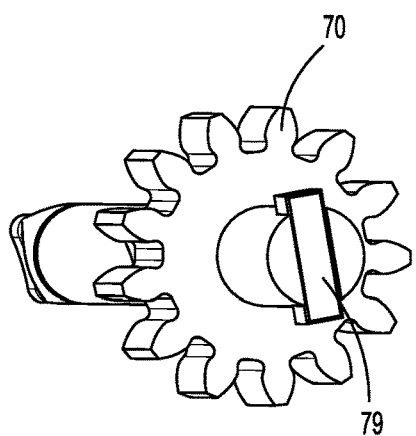
FIG. 32
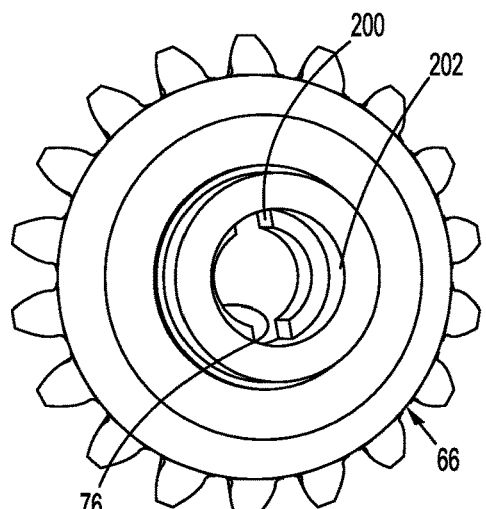
FIG. 32A
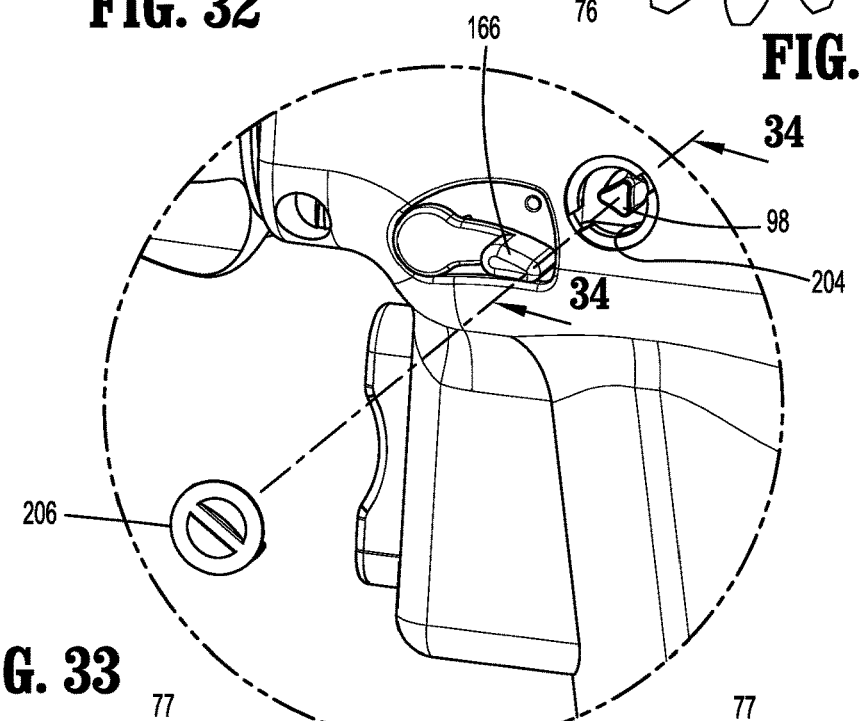
FIG. 33
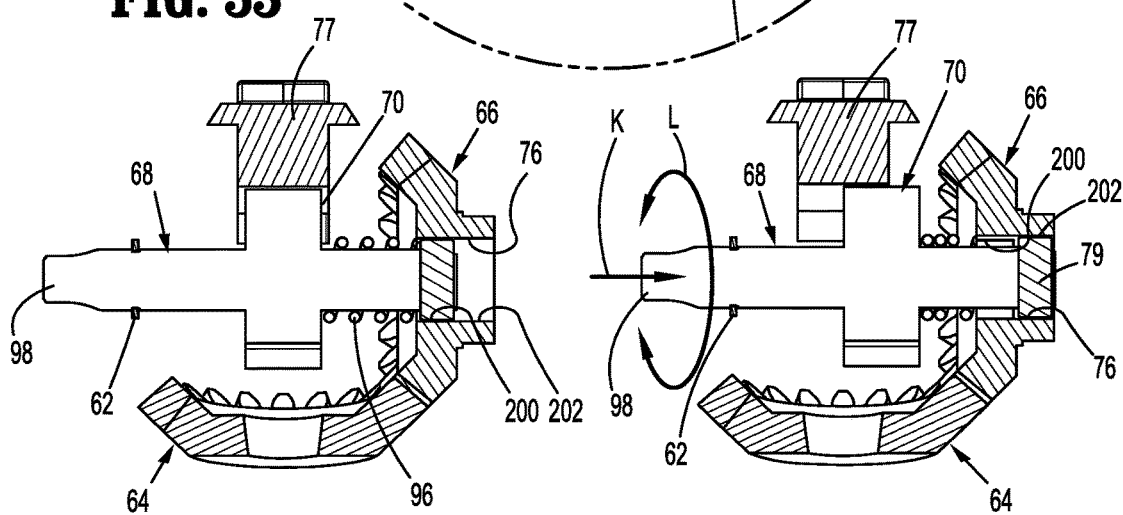
FIG. 34  FIG. 35

SURGICAL STAPLING DEVICE WITH POWERED HANDLE ASSEMBLY

CROSS REFERENCE TO RELATED APPLICATIONS

This application is a continuation of U.S. application Ser. No. 17/279,836, filed Mar. 25, 2021, which is a National Stage Application of PCT Application No. PCT/CN2018/110427 under 35 U.S.C. § 371(a), filed Oct. 16, 2018, the disclosures of each of which are hereby incorporated by reference in their entirety.

BACKGROUND

1. Technical Description

The present disclosure is directed to a powered handle assembly for a surgical stapling device and, more particularly, to a powered handle assembly for a linear surgical stapling device that can be used with staple reloads of different lengths.

2. Background of Related Art

Linear surgical stapling devices for performing anastomoses are well known. Typically, a linear stapling device includes a staple reload having a staple cartridge that includes a plurality of rows of staples and a knife that is movable between the rows of staples. The staple cartridge is available in a variety of different lengths, e.g., 15 mm, 30 mm, 45 mm, and 60 mm. In some devices, the staple reload is coupled to a powered handle assembly and can be replaced with a fresh staple reload after the staple cartridge is spent to facilitate reuse of the handle assembly.

In some instances, it may be desirable to use a single handle assembly to fire staple reloads of different sizes. As such, such devices must include structure that is capable of adjusting a stroke length of a drive member of the stapling device to accommodate the staple cartridges of different lengths. This structure may be complex and costly.

A continuing need exists in the art for a surgical stapling device that includes a simple and economic mechanism that can control the stroke length of a powered stapling device to allow a powered handle assembly of the stapling device to fire staple reloads that have different length staple cartridges.

SUMMARY

One aspect of the present disclosure is directed to a surgical stapling device including a handle assembly, a motor assembly, a drive rack, a tool assembly, and a gear assembly. The handle assembly includes a housing defining a stationary grip and supporting a trigger. The motor assembly is supported within the housing. The drive rack is also supported within the housing and is movable within the housing between an advanced position and a retracted position. The tool assembly includes a cartridge assembly and an anvil assembly. The cartridge assembly includes a staple cartridge that supports a plurality of staples. The cartridge assembly is movable in relation to the anvil assembly to move the tool assembly between an open position and a clamped position. The gear assembly is supported within the housing of the handle assembly between the motor assembly and the drive rack and includes a first bevel gear that is engaged with the motor assembly, a transmission shaft, a second bevel gear engaged with the first bevel gear and supported on the transmission shaft, and a pinion fixedly supported on the transmission shaft that is engaged with the rack. The transmission shaft is movable in relation to the second bevel gear from a first position in which the transmission shaft is rotatably fixed to the second bevel gear and a second position in which the transmission shaft is rotatable independently of the second bevel gear. In the first position of the transmission shaft, rotation of the first bevel gear causes rotation of the second bevel gear, to rotate the pinion move the drive rack longitudinally. In the second position of the transmission shaft, the transmission shaft is rotatable independently of the second bevel gear such that the transmission shaft can be manually rotated to move the drive rack longitudinally within the housing independently of the motor assembly.

Another aspect of the present disclosure is directed to a powered handle assembly including a housing, a motor assembly, a drive rack, and a gear assembly. The motor assembly and the drive rack are supported within the housing and the drive rack is movable within the housing between an advanced position and a retracted position. The gear assembly is supported within the housing of the handle assembly between the motor assembly and the drive rack. The gear assembly includes a first bevel gear that is engaged with the motor assembly, a transmission shaft, a second bevel gear engaged with the first bevel gear and supported on the transmission shaft, and a pinion fixedly supported on the transmission shaft and engaged with the rack. The transmission shaft is movable in relation to the second bevel gear from a first position in which the transmission shaft is rotatably fixed to the second bevel gear and a second position in which the transmission shaft is rotatable independently of the second bevel gear. In the first position of the transmission shaft, rotation of the first bevel gear causes rotation of the second bevel gear to rotate the pinion to cause longitudinal movement of the drive rack. In the second position of the transmission shaft, the transmission shaft is rotatable independently of the second bevel gear such that the transmission shaft can be manually rotated to move the drive rack longitudinally within the housing independently of the motor assembly.

In embodiments, the gear assembly includes a biasing member positioned to urge the transmission shaft to the second position.

In some embodiments, the biasing member is positioned between the pinion and the second bevel gear.

In certain embodiments, the biasing member includes a coil spring.

In embodiments, the transmission shaft includes an engagement end and the housing defines an access opening that is positioned and configured to provide access to the engagement end of the transmission shaft to facilitate movement of the transmission shaft between the first and second positions.

In some embodiments, the engagement end of the transmission shaft is configured to engage a tool to facilitate manual rotation of the transmission shaft.

In certain embodiments, the engagement end of the transmission shaft has a non-circular configuration.

In embodiments, the housing of the handle assembly includes a cover that is received within the access opening to close the access opening, and the cover is removable from the access opening to provide access to the transmission shaft.

In some embodiments, the transmission shaft includes a key and the second bevel gear defines a central bore having a first portion that has a shape that corresponds to the key and a second portion that is configured to permit rotation of the key within the central bore, wherein the key is positioned within the first portion of the central bore in the first position of the transmission shaft and the key is positioned in the second portion of the central bore when the transmission shaft is in the second position.

In certain embodiments, the gear assembly includes a gear housing having a first side defining a bore and a second opposite side defining a circular cutout, and the transmission shaft has a first end extending through the bore in the first side of the gear housing and a second end supported by the second bevel gear, wherein the second bevel gear includes a hub that is rotatably supported within the circular cutout in the second opposite side of the gear housing such that the transmission shaft, the second bevel gear, and the pinion are rotatably supported within the gear housing.

In embodiments, the gear housing includes outwardly extending protrusions and the housing of the handle assembly defines slots, wherein the slots are configured to receive the protrusions to locate and secure the gear housing within the housing of the handle assembly.

In some embodiments, the motor assembly includes a motor and a gearbox.

In certain embodiments, the gear housing is secured to the gearbox of the motor assembly with a mounting plate.

In embodiments, a control rod has a proximal end coupled to the drive rack and a distal end coupled to the reload, wherein longitudinal movement of the drive rack causes corresponding longitudinal movement of the control rod to control operation of the reload.

Another aspect of the present disclosure is directed to a surgical stapling device including a handle assembly, a motor assembly, a drive rack, a tool assembly, and a safety toggle mechanism. The handle assembly includes a housing defining a stop and a cavity and supporting a trigger. The housing includes a switch positioned within the cavity that is movable from a non-depressed state to a depressed state. The motor assembly is supported in the cavity of the housing. The drive rack is supported within the cavity of the housing and is movable between an advanced position and a retracted position. The tool assembly includes a cartridge assembly and an anvil assembly. The cartridge assembly includes a staple cartridge that supports a plurality of staples and is movable in relation to the anvil assembly to move the tool assembly between an open position and a clamped position. The safety toggle mechanism includes a shaft having first and second ends, a retaining member, and at least one toggle. The shaft is rotatably supported within the cavity of the housing and includes an abutment member that positioned adjacent the switch. The shaft is rotatable between a first position in which the switch is in the non-depressed state and a second position in which the abutment is engaged with the switch and the switch is in the depressed state. The at least one toggle is secured to the first end of the shaft and is positioned externally of the cavity of the housing such that the at least one toggle can be manually rotated to rotate the shaft between the first and second positions, wherein the retaining member is supported on the shaft and is movable into engagement with the stop when the shaft is rotated from the first position to the second position to retain the shaft in the second position.

Another aspect of the present disclosure is directed to a safety toggle mechanism including a shaft, a retaining mechanism, and at least one toggle. The shaft defines a longitudinal axis and has first and second ends and supports an abutment member. The abutment member is rotatably fixed to the shaft such that rotation of the shaft causes corresponding rotation of the abutment member. The retaining member is rotatably fixed to the shaft and is axially movable along the shaft between first and second positions. The at least one toggle is secured to the first end of the shaft such that the at least one toggle can be manually rotated to rotate the shaft.

In embodiments, the at least one toggle includes a first toggle and a second toggle, wherein the first toggle is supported on the first end of the shaft on one side of the housing and the second toggle is supported on a second end of the shaft on a second side of the housing.

In some embodiments, the retaining member is rotatably fixed to the shaft such that rotation of the shaft causes corresponding rotation of the retaining member.

In certain embodiments, the stop includes a proximal side defining a stop surface and the retaining member is movable along the shaft from a first position to a second position to allow the retaining member to pass over the stop and move into engagement with the stop surface.

In embodiments, the shaft defines a channel and the retaining member includes a hub that defines a bore that receives the shaft.

In certain embodiments, the hub includes a tab that extends into the bore such that the tab is received within the channel of the shaft, wherein the channel is dimensioned to allow movement of the retaining member along the shaft between its first and second positions.

In some embodiments, the safety toggle assembly further includes a biasing member that is positioned to urge the retaining member towards the first position.

In certain embodiments, the biasing member includes a coil spring.

In embodiments, the safety toggle assembly includes a biasing member to urge the shaft towards its first position.

In embodiments, the biasing member is a torsion spring that is positioned between the abutment and the housing.

Yet another aspect of the present disclosure is directed to a handle assembly for a surgical device including a housing, a motor supported within the housing, a trigger operably coupled to the motor, a drive rack, a switch, and a reload select mechanism. The drive rack is operably engaged with the motor, includes an engagement surface, and is movable between retracted and advanced positions in response to activation of the motor. The switch is operably associated with the motor and is movable between a non-firing state and a firing state to control operation of the motor and longitudinal movement of the drive rack. The reload select mechanism has a plurality of actuator assemblies including a first actuator assembly and a second actuator assembly. Each of the plurality of actuator assemblies is longitudinally spaced from each other along the housing and is independently movable into alignment with the engagement surface of the drive rack. Each of the plurality of actuator assemblies is operably associated with the switch such that engagement of the engagement surface of the drive rack with the first actuator assembly moves the switch from the firing state to the non-firing state to disable the motor and define a first drive rack stroke having a first length and engagement of the engagement surface of the drive rack with the second actuator assembly moves the switch from the firing state to the non-firing state to disable the motor and define a second drive rack stroke having a second length, wherein the first length is less than the second length.

Another aspect of the present disclosure is directed to a surgical stapling device including an elongate body, a staple reload, and a tool assembly. The elongate body has a proximal portion and a distal portion and supports a control rod. The staple reload is supported on the distal portion of the elongate body and includes an anvil assembly and a staple cartridge that supports a plurality of staples. The control rod is coupled to the reload and is movable between retracted and advanced positions to eject the plurality of staples from the staple cartridge. The handle assembly is coupled to the proximal portion of the elongate body and includes a housing, a motor supported within the housing, a trigger operably coupled to the motor, a drive rack, a switch, and a reload select mechanism. The drive rack is operably engaged with the motor, includes an engagement surface, and is movable between retracted and advanced positions in response to activation of the motor to move the control rod between its retracted and advanced positions. The switch is operably associated with the motor and is movable between a non-firing state and a firing state to control operation of the motor and longitudinal movement of the drive rack. The reload select mechanism has a plurality of actuator assemblies including a first actuator assembly and a second actuator assembly. Each of the plurality of actuator assemblies is longitudinally spaced from each other along the housing and is independently movable into alignment with the engagement surface of the drive rack. Each of the plurality of actuator assemblies is operably associated with the switch such that engagement of the engagement surface of the drive rack with the first actuator assembly moves the switch from the firing state to the non-firing state to disable the motor and define a first drive rack stroke having a first length and engagement of the engagement surface of the drive rack with the second actuator assembly moves the switch from the firing state to the non-firing state to disable the motor and define a second drive rack stroke having a second length, wherein the first length is less than the second length.

In embodiments, each of the plurality of actuator assemblies is movable from an initial state to an actuated state to move the switch from the non-firing state to the firing state.

In some embodiments, each of the plurality of actuator assemblies includes an actuator and a retainer, the retainer being supported on the actuator and positioned to engage the drive rack when the respective one of the plurality of actuator assemblies is in the actuated position.

In embodiments, each of the retainers is configured to retain a respective one of the plurality of actuator assemblies in the actuated position.

In certain embodiments, the housing defines a plurality of guide slots and each of the guide slots includes an abutment including a retaining wall, wherein each of the retainers has a guide member that is received in a respective one of the plurality of guide slots, and the guide member is movable into engagement with the retaining wall of the respective abutment to retain the respective one of the actuator assemblies in the actuated position.

In embodiments, the retaining wall defines a concavity that is positioned to receive the guide member of the retainer of the respective one of the plurality of actuator assemblies.

In some embodiments, each of the plurality of actuator assemblies includes a biasing member that is positioned to urge the respective one of the plurality of actuator assemblies towards the initial position.

In certain embodiments, a slide member positioned between the switch and the plurality of actuator assemblies, wherein the slide member is movable between a first position in which the switch is in the non-firing state and a second position engaged with the switch in which the switch is in the firing state.

In embodiments, the actuator of each of the plurality of actuator assemblies includes a cam member and the slide member includes a cam slot associated with each of the plurality of actuator assemblies, wherein each of the cam slots is defined by a cam surface and the cam member of each of the plurality of actuator assemblies is positioned to engage a respective cam surface of the clamp slide in response to movement of one of the plurality of actuator assemblies from the initial position to the actuated position to move the slide member from the first position to the second position.

In some embodiments, the slide member includes a locking member associated with each of the cam slots and the cam member of each of the plurality of actuator assemblies defines a notch, wherein each of the locking members is received within the notch of the cam member of the respective one of the plurality of actuator assemblies in the initial position when the slide member is in the second position to prevent movement of the other of the plurality of actuator assemblies from the initial state to the actuated state.

BRIEF DESCRIPTION OF THE DRAWINGS

Various embodiments of the presently a surgical stapling device with the presently disclosed powered handle assembly are described herein below with reference to the drawings, wherein:

FIG. 26 is a side perspective, exploded view of the safety toggle assembly shown in FIG. 25;

FIG. 27 is a side perspective view from the distal end of the portion of the handle assembly supporting the safety toggle mechanism shown in FIG. 26 with the safety toggle mechanism in a clamping state;

FIG. 28 is a side perspective view from the proximal end of the portion of the handle assembly shown in FIG. 27 with the safety toggle mechanism in the clamping state;

FIG. 32 is a side perspective view of a transmission shaft and pinion of the gear assembly shown in FIG. 8;

FIG. 32A is a side perspective view of the second bevel gear of the gear assembly shown in FIG. 8;

FIG. 33 is an enlarged view of the area of detail shown in FIG. 2 with an access cover to the transmission shaft removed from an access opening in the housing of the handle assembly;

FIG. 34 is a cross-sectional view taken along section line 34-34 of FIG. 33; and FIG. 35 is a side cross-sectional view taken along section line 34-34 of FIG. 33 with the transmission shaft disengaged with the second bevel gear.

DETAILED DESCRIPTION OF EMBODIMENTS

Figure 1:
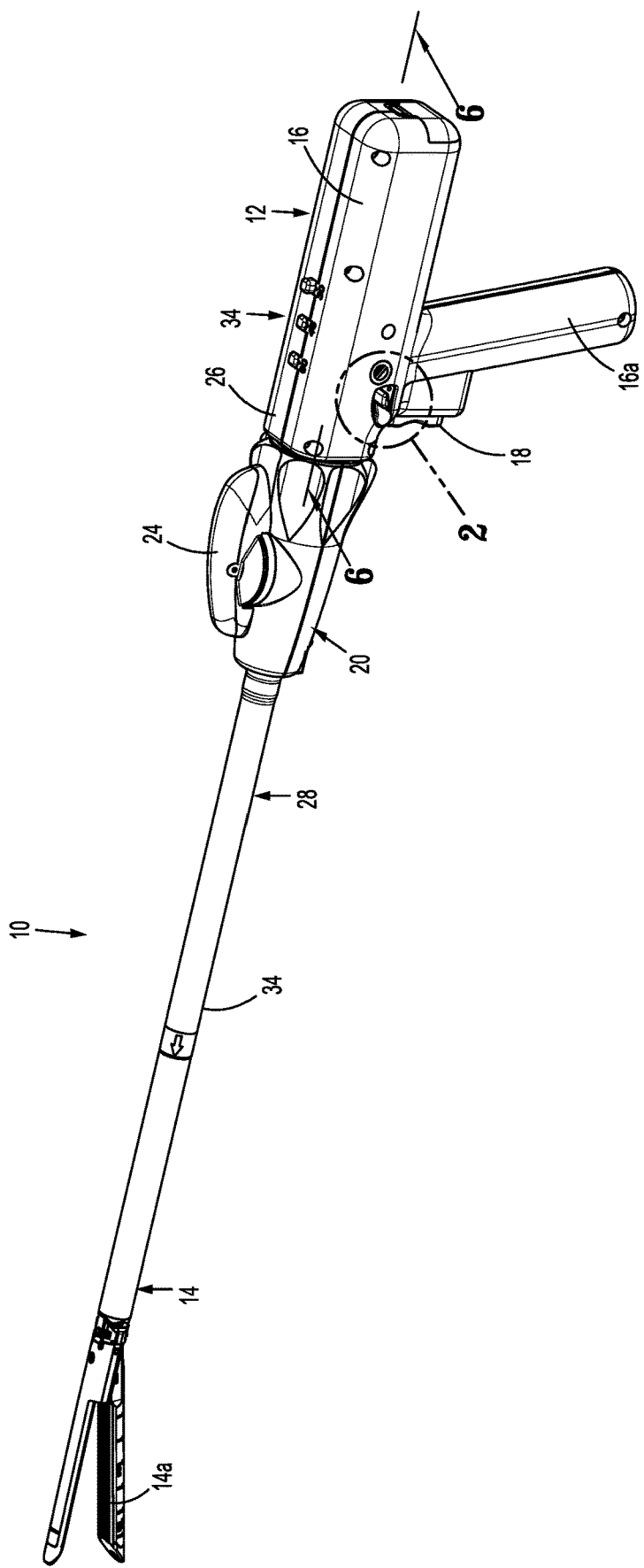
FIG. 1 is a side perspective view of an exemplary embodiment of the presently disclosed surgical stapling device with a tool assembly of a staple reload of the stapling device in an unclamped position.

The presently disclosed surgical stapling device with a powered handle assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

Figure 2:
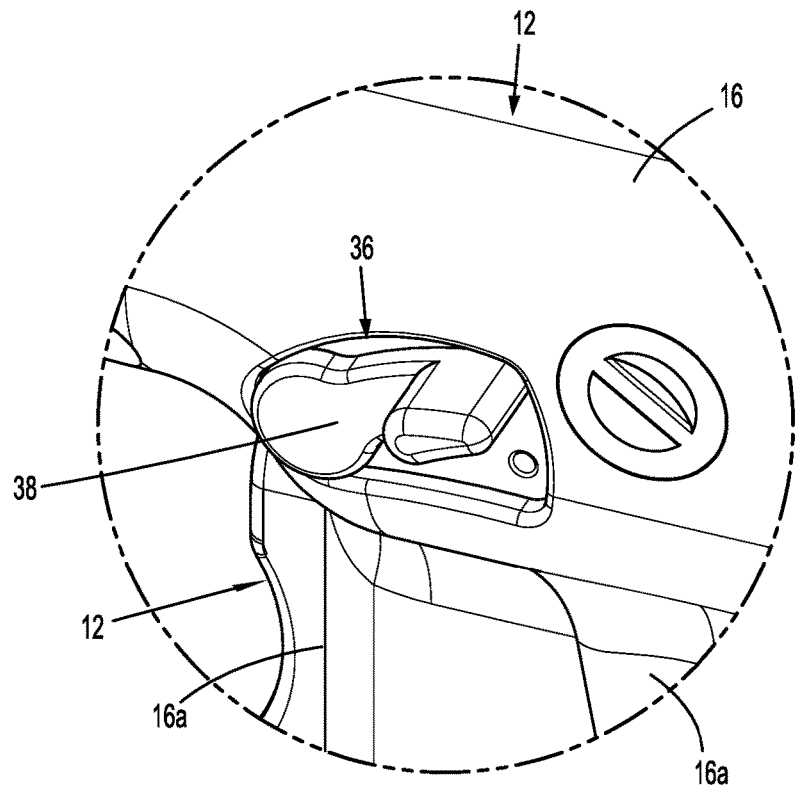
FIG. 2 is an enlarged view of the indicated area of detail shown in FIG. 1.
Figure 3:
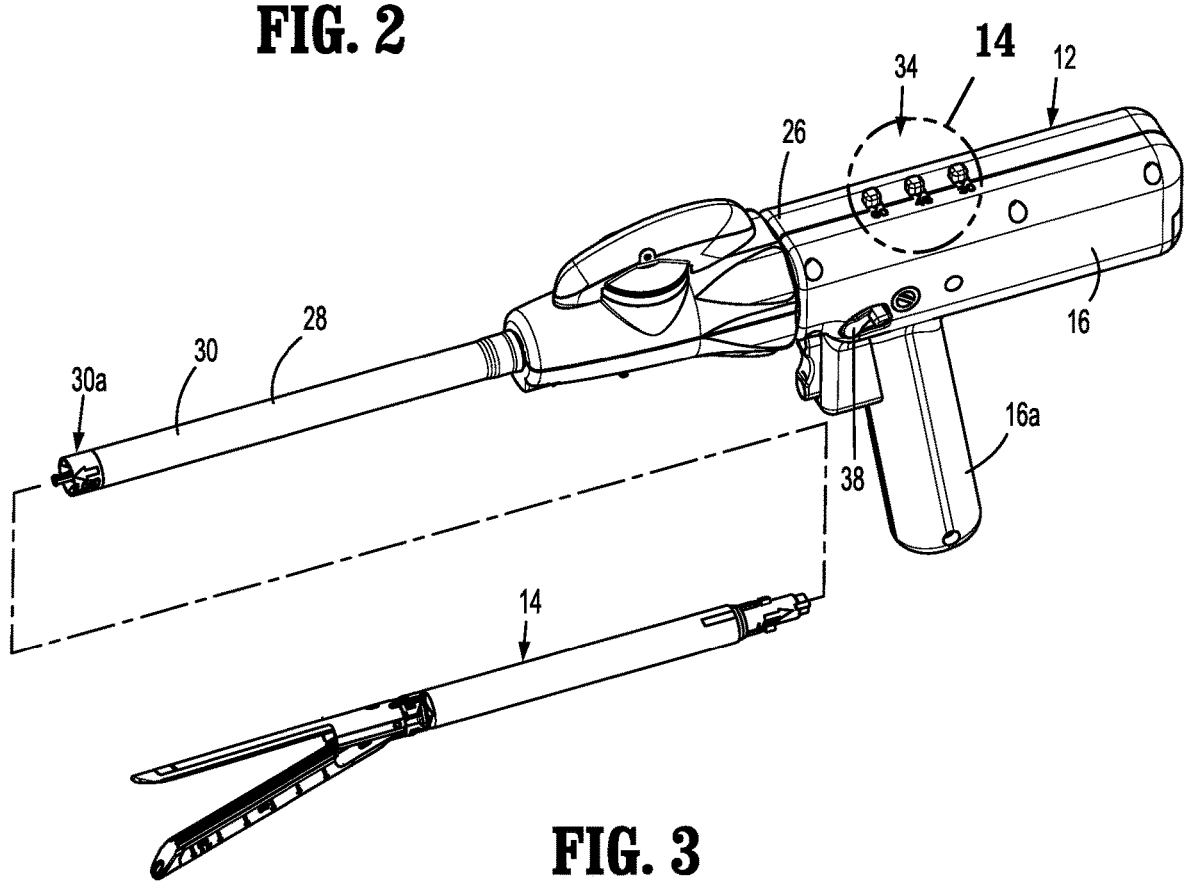
FIG. 3 is a side perspective view of the stapling device shown in FIG. 1 with the staple reload separated from a handle assembly of the stapling device.
Figure 4:
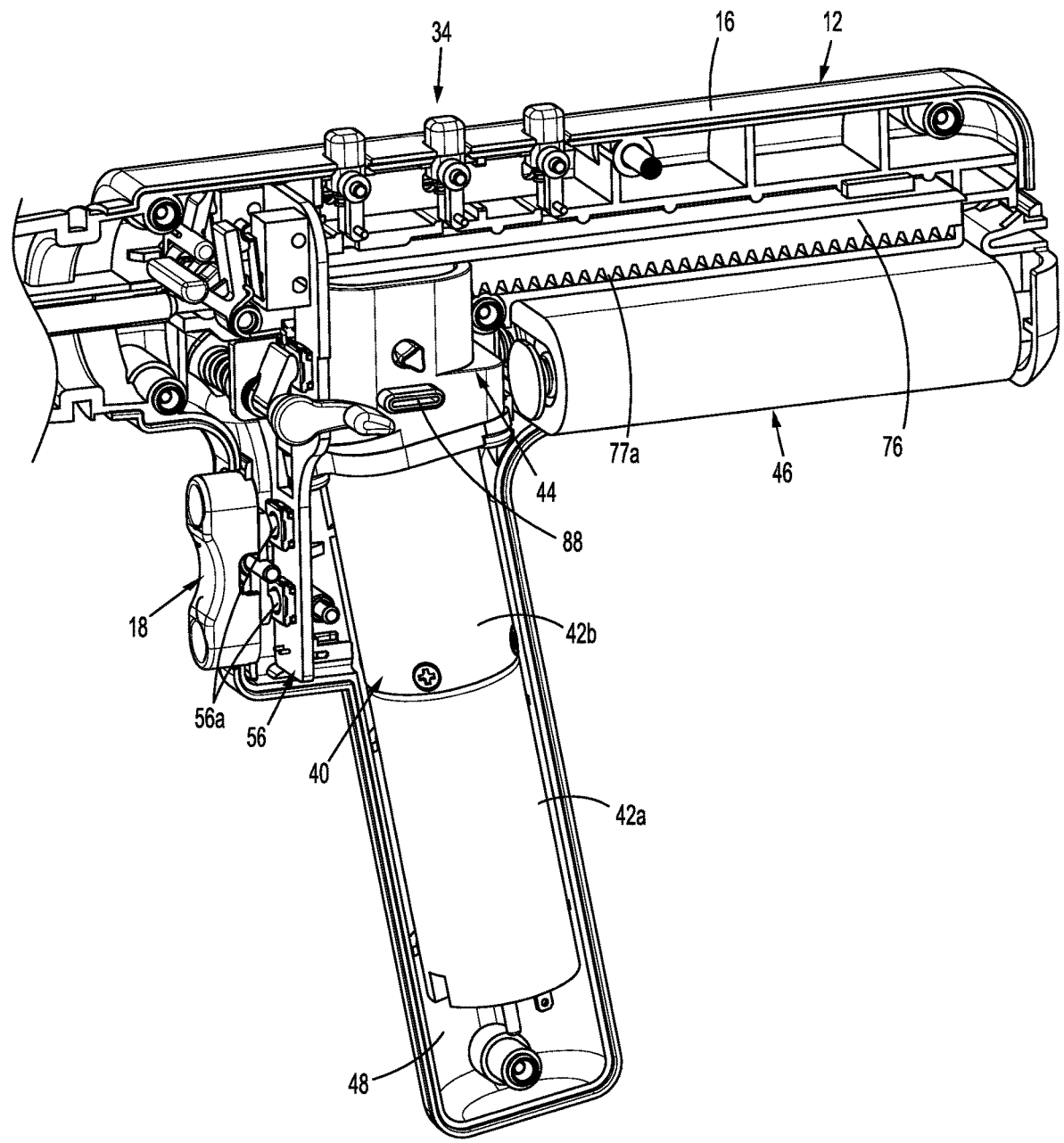
FIG. 4 is side perspective view of the handle assembly of the stapling device shown in FIG. 3 with a housing half-section removed.

Referring to FIGS. 1-3, the presently disclosed surgical stapling device is shown generally as 10 and includes a handle assembly 12 and a staple reload 14. In embodiments, the staple reload 14 includes a tool assembly 14a and a proximal body portion 14b. The tool assembly 14a has a cartridge assembly 15a that supports a staple cartridge 17, and an anvil assembly 15b. The anvil assembly 15b is movable in relation to the cartridge assembly 15a such that the tool assembly 14a is movable between an open position and a clamped position.

The handle assembly 12 includes a housing 16 defining stationary grip 16a, a trigger 18 supported on the housing 16 that can be depressed to activate the handle assembly 12, a rotation knob 20, and an articulation lever 24 supported on the rotation knob 20. In embodiments, the rotation knob 20 is supported on a distal portion 26 of the housing 16 of the handle assembly 12 and can be rotated about a longitudinal axis of the staple reload 14 to rotate the staple reload 14 in relation to the housing 16 of the handle assembly 12. The stapling device 10 also includes an elongate body 28 having a proximal portion supported on the housing 16 of the handle assembly 12 and a distal portion 30 including structure 30a (FIG. 3) to releasably couple the elongate body 28 to the staple reload 14. For a more detailed description of a surgical stapling device that includes a staple reload and structure to releasably couple the staple reload to a handle assembly, see U.S. Pat. No. 7,565,993 ("'993 Patent'") and U.S. Pat. No. 9,931,683 ("'683 Patent") that are incorporated herein in their entirety by reference.

Figure 25:
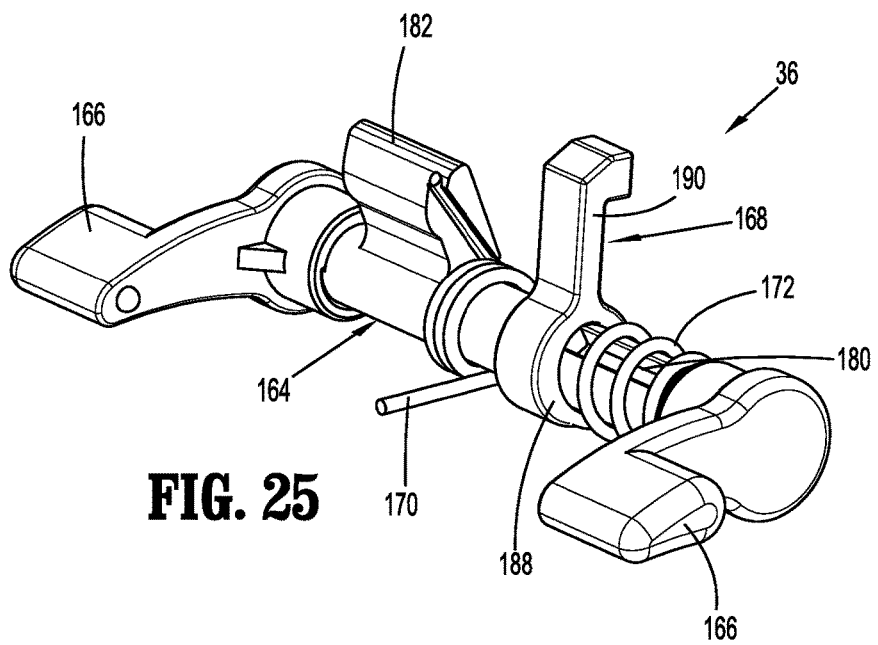
FIG. 25 is a side perspective view of a safety toggle assembly of the handle assembly of the stapling device shown in FIG. 1.

The handle assembly 12 also includes a staple reload select mechanism 34 (FIG. 12) and a safety toggle assembly 36 (FIG. 25). The staple reload select mechanism 34 can be selectively actuated to allow a clinician to control a length of a firing stroke of the handle assembly 12 to facilitate use of the handle assembly 12 with staple reloads 14 having different length staple cartridges 15 as described in further detail below. The safety toggle mechanism 36 includes a toggle 38 that is movably supported on the housing 16 of the handle assembly 12 to activate the handle assembly 12 for firing of the stapling device 10 after the stapling device 10 is in a clamped position as will also be described in further detail below.

Figure 5:
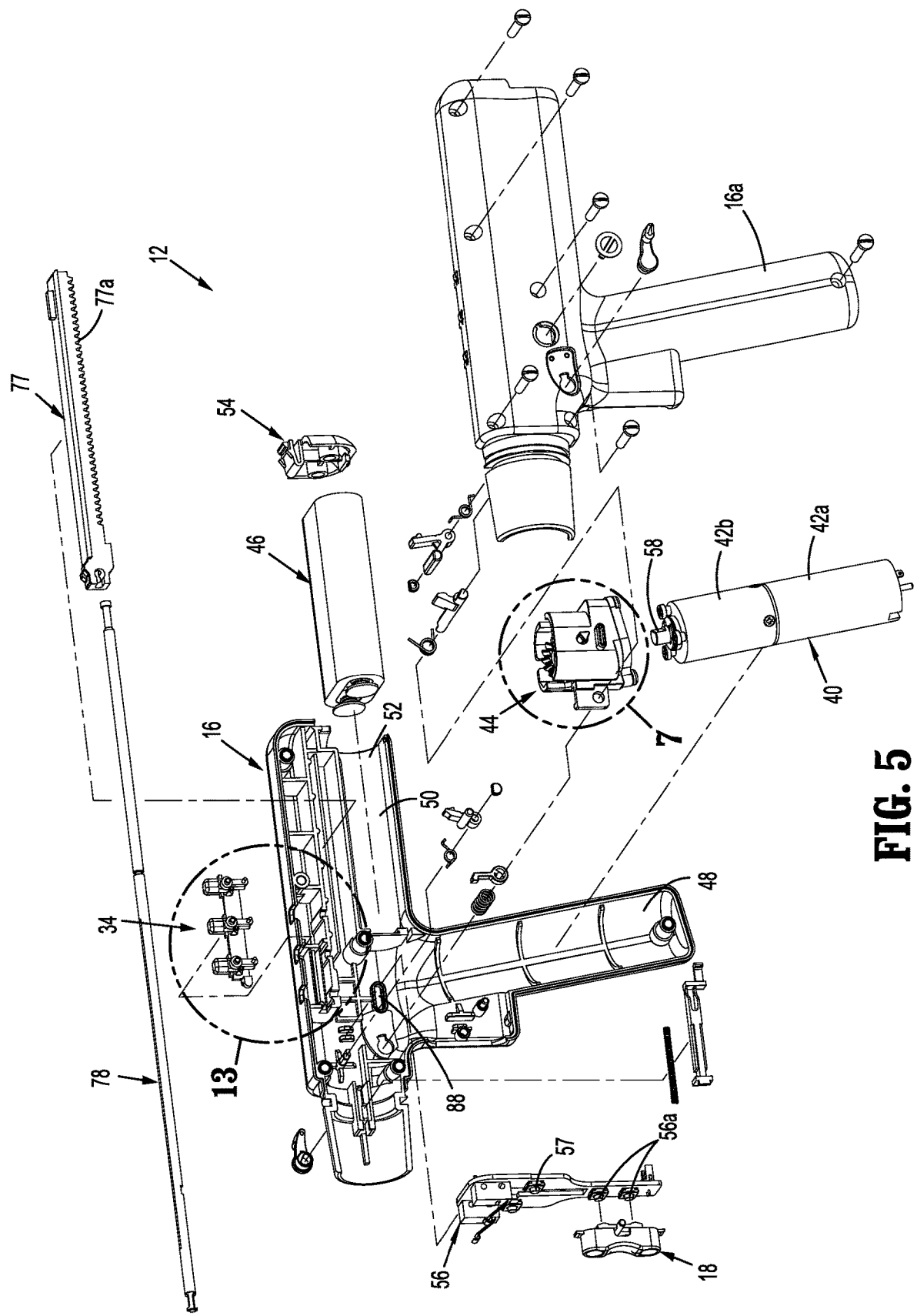
FIG. 5 is an exploded view of the handle assembly shown in FIG. 3.
Figure 6:
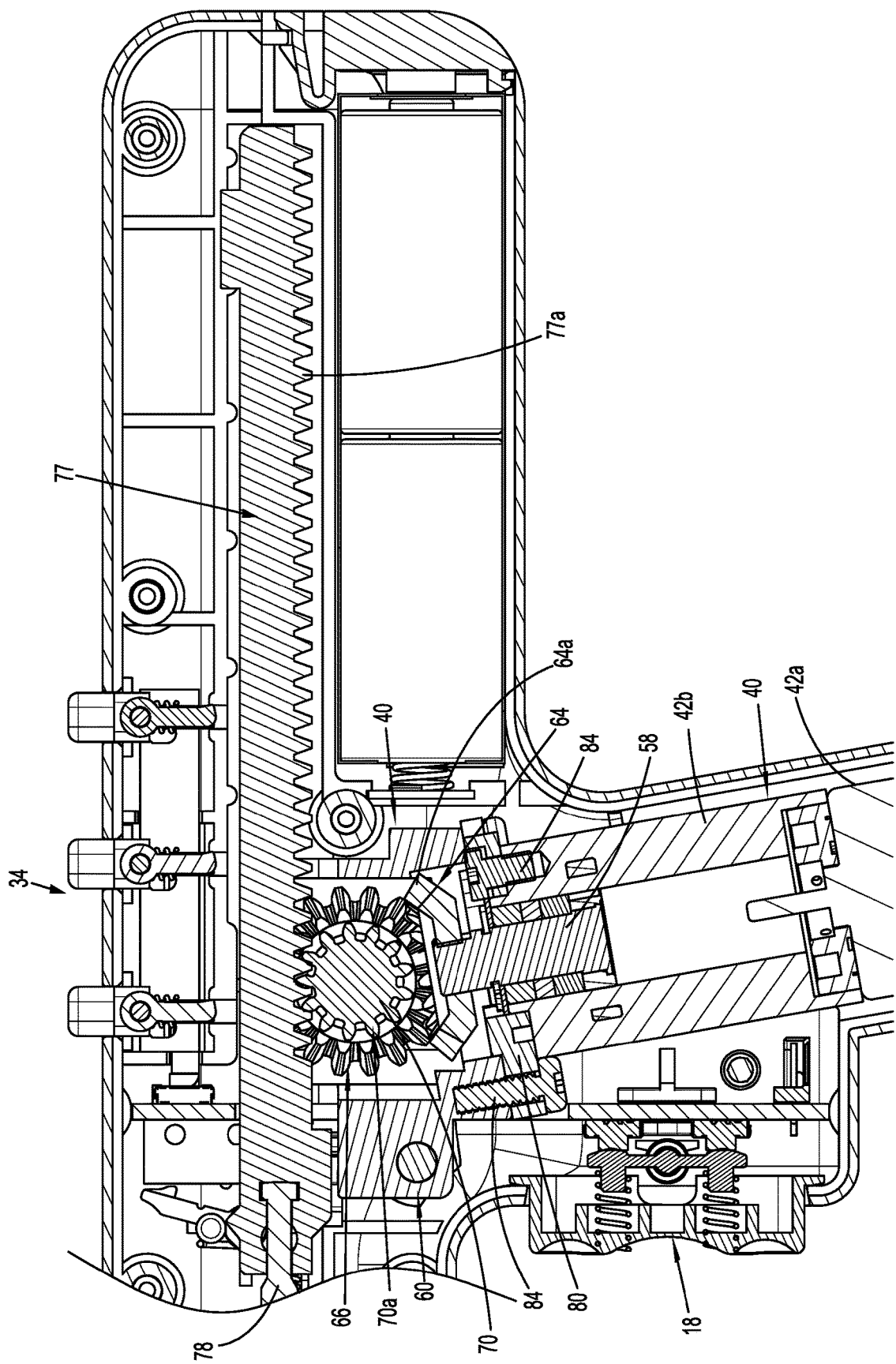
FIG. 6 is a cross-sectional view taken along section line 6-6 of FIG. 1.
Figure 8:
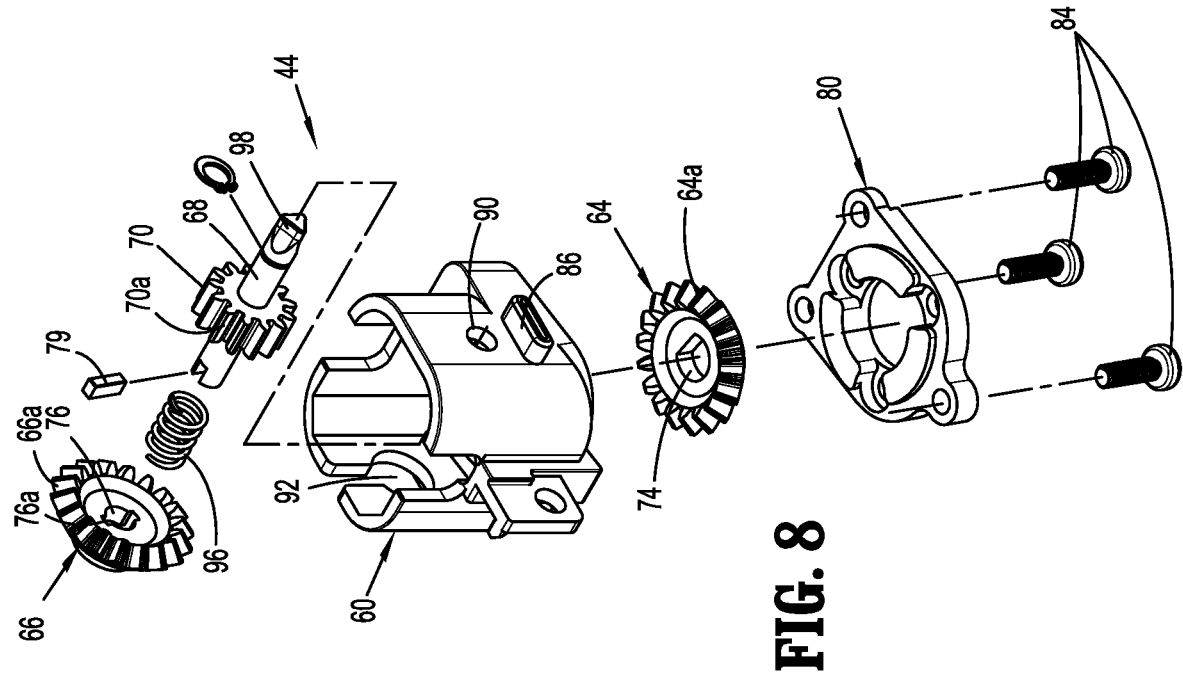
FIG. 8 is an exploded view of the gear assembly shown in FIG. 7.
Figure 7:
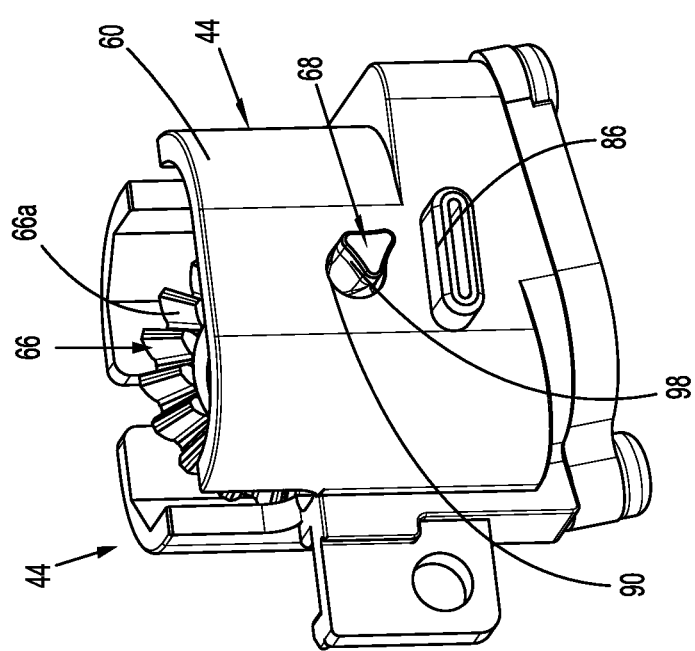
FIG. 7 is an enlarged view of the indicated area of detail shown in FIG. 5.
Figure 9:
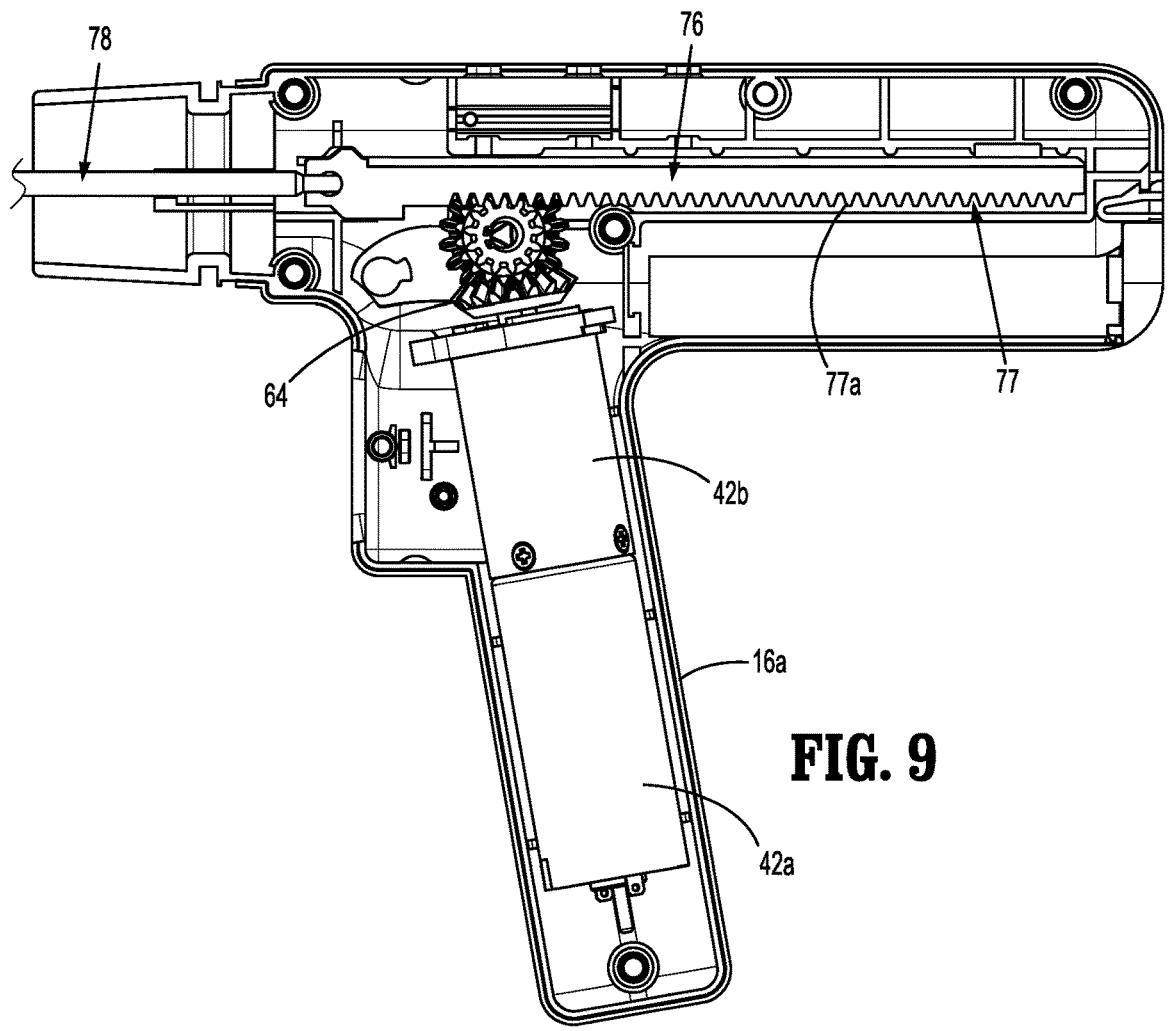
FIG. 9 is a side view of the handle assembly shown in FIG. 3 with the housing half-section of the handle assembly and a housing of the gear assembly removed.
Figure 10:
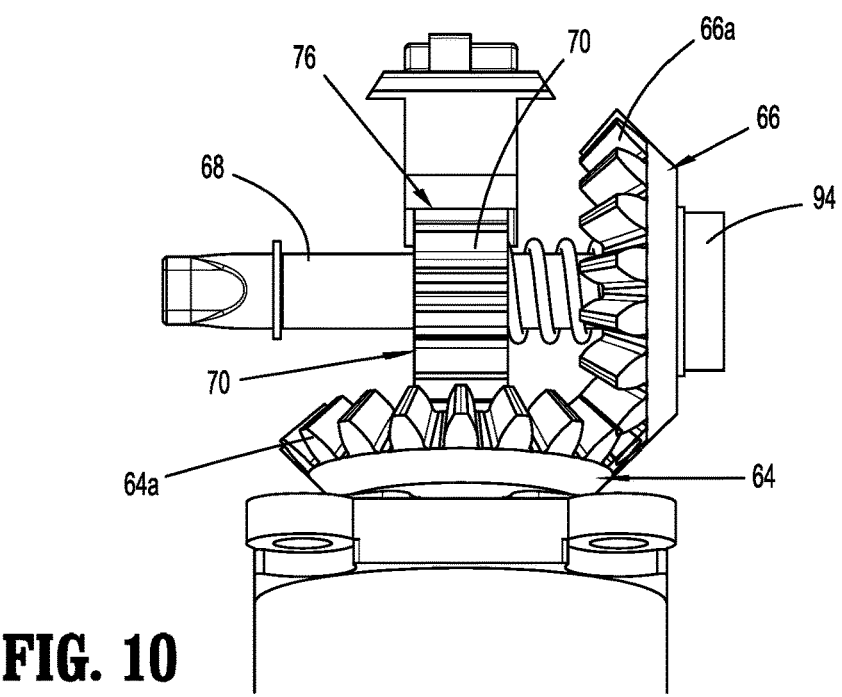
FIG. 10 is a perspective view from the proximal end of the gear assembly shown in FIG. 8 with the housing of the gear assembly removed.
Figure 11:
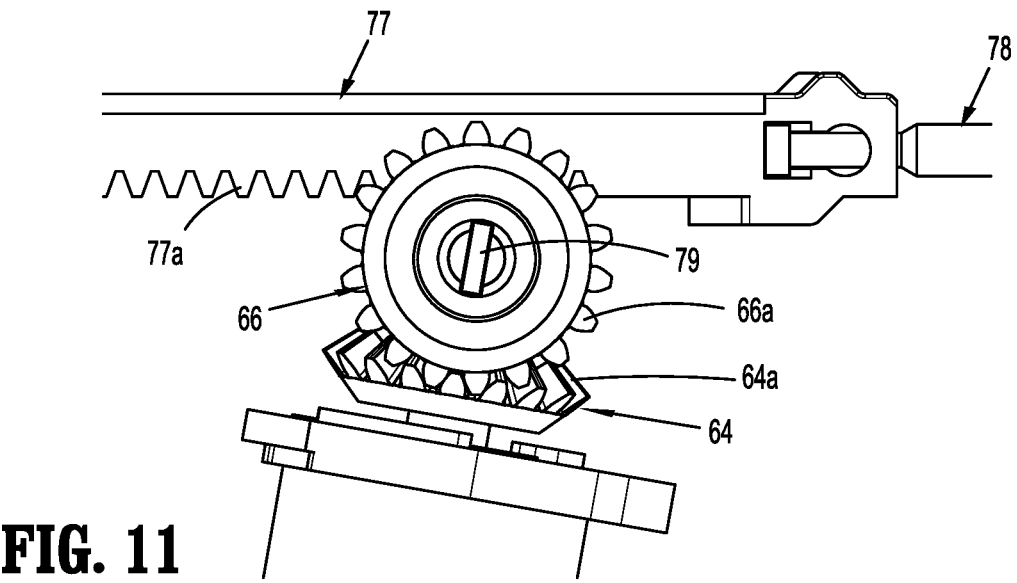
FIG. 11 is a side view of the gear assembly and rack of the handle assembly shown in FIG. 9 with the gear assembly housing removed.

Referring to FIGS. 4-11, the handle assembly 12 includes a motor assembly 40, a gear assembly 44, and batteries 46. The motor assembly 40 includes a motor 42a and a gearbox 42b. In embodiments, the housing 16 of the handle assembly 12 defines a first cavity 48 (FIG. 5) and a second cavity 50 (FIG. 5). The first cavity 48 is defined within the stationary grip 16a and receives the motor assembly 40 and the second cavity 50 is defined within a proximal portion of the housing 16 and receives the batteries 46. The proximal portion of the housing 16 defines an opening 52 (FIG. 5) that is closed by a cover 54 coupled to the housing 16. The cover 54 is adapted to be selectively removed from the housing 16 to uncover the opening 52 (FIG. 5) provide access to the second cavity 50 of the housing 16. The housing 16 also supports a printed circuit board ("PCB") 56 that provides an electrical path between the batteries 46 and the motor assembly 40 via the trigger 18. The PCB 56 supports a number of switches 56a (FIG. 4) and 57 (FIG. 5) that can be actuated via the trigger 18 to selectively provide power to the motor assembly 40 to effect the clamping and stapling functions of the stapling device 10.

The gearbox 42b of the motor assembly 40 includes an output drive shaft 58 (FIG. 5) that is coupled to the gear assembly 44. The gear assembly 44 (FIG. 8) includes a housing 60, a first bevel gear 64 including gear teeth 64a, a second bevel gear 66 including gear teeth 66a, a transmission shaft 68, and a pinion 70 including gear teeth 70a. The first bevel gear 64 is coupled to the output drive shaft 58 (FIG. 5) of the motor assembly 40. In embodiments, the output drive shaft 58 has a D-shaped configuration and the first bevel gear 64 includes a D-shaped bore 74 (FIG. 8) that receives the output drive shaft 58 to fix the first bevel gear 64 to the output drive shaft 58 such that rotation of the output drive shaft 58 causes rotation of the first bevel gear 64.

The gear teeth 64a of the first bevel gear 64 are engaged with the gear teeth 66a of the second bevel gear 66. When the output drive shaft 58 of the motor assembly 40 is activated, rotation of the output drive shaft 58 causes the first bevel gear 64 to rotate which in turn causes the second bevel gear 66 to rotate. The second bevel gear 66 is secured to the transmission shaft 68 with a key 79 (FIG. 8) that is fixedly connected to the transmission shaft 68. In embodiments, the second bevel gear 66 defines a central bore 76 having a first portion 200 (FIG. 32A) that has a shape that corresponds to the shape of the key 79 and a second portion 202 (FIG. 32A) that is configured to permit rotation of the key 79 within the central bore 76 independently of the second bevel gear 66. When the key 79 is received in the first portion 200 of the central bore 76 of the second bevel gear 66, rotation of the bevel gear 66 causes rotation of the transmission shaft 68. However, when the key 79 is received in the second portion 202 of the central bore 76 of the second bevel gear 66, rotation of the second bevel gear 66 will not cause rotation of the transmission shaft 68, nor will rotation of the transmission shaft 68 cause rotation of the second bevel gear 66 as described in further detail below.

The pinion 70 is secured to a central portion of the transmission shaft 68 and is positioned to engage a drive rack 77 supported within the housing 16 of the handle assembly 12. The drive rack 77 includes teeth 77a (FIG. 9) that mesh with the gear teeth 70a of the pinion 70. When the transmission shaft 68 is rotated in response to activation of the motor assembly 40, engagement between the gear teeth 70a and the gear teeth 77a of the drive rack 77 causes longitudinal movement of the drive rack 77 within the housing of the handle assembly 12 between a retracted position and an advanced position. The distance of travel or stroke of the drive rack 77 is defined by the reload select mechanism 34 and varies depending on the stroke selected by the reload select mechanism 34 as described below. The drive rack 77 includes a distal end that that is coupled to a control rod 78 (FIG. 9) of the handle assembly 12. The control rod 78 includes a distal end that is adapted to engage a drive assembly (not shown) of the staple reload 14 when the staple reload 14 is coupled to the elongate body 28 of the handle assembly 12 such that longitudinal advancement of the control rod 78 actuates the staple reload 14. For a detailed description of the interconnection between the drive rack 77, the control rod 78, and the staple reload 14, see the '993 Patent.

The housing 60 of the gear assembly 44 is supported within the housing 16 of the handle assembly 12 at a position adjacent the stationary grip 16a. A mounting plate 80 is secured to the housing 60 between the motor assembly 40 and the housing 60 using screws 84 to mount the gear assembly 44 to the motor assembly 40. Opposite side walls of the housing 60 of the gear assembly 44 include elongated protrusions 86 (FIG. 7) that are received in slots 88 (FIG. 5) defined within the housing 12 of the handle assembly 12 to properly locate and secure the housing 60 of the gear assembly 44 within the housing 16 of the handle assembly 12.

The housing 60 of the gear assembly 44 includes a first side defining a bore 90 (FIG. 8) and a second opposite side defining a circular cutout 92. The bore 90 receives one end portion of the transmission shaft 68 and the circular cutout 92 receives a hub 94 (FIG. 10) of the second bevel gear 66 such that the second bevel gear 66 and the transmission shaft 68 are rotatably supported within the housing 60 of the gear assembly 44. In embodiments, the gear assembly 44 includes a biasing member, e.g., a coil spring 96, positioned between the pinion gear 70 and an inner surface of the second bevel gear 66 to urge the pinion gear 70 and the transmission shaft 68 towards the bore 90 such that an engagement end 98 of the transmission shaft 68 projects through the bore 90 (FIG. 7) in the housing 60 of the gear assembly 44. As described in further detail below, the engagement end 98 of the transmission shaft 68 is shaped to be engaged with a tool (not shown) to facilitate manual advancement of the drive rack 77. In some embodiments, engagement end 98 of the transmission shaft 68 is triangular. Alternately, other configurations are envisioned. As described in further detail below, the end of the transmission shaft 68 opposite to the engagement end 98 of the transmission shaft 68 that supports the key 79 extends through the second bevel gear 66 and is movable against the bias of the spring 96 to move the key 79 into and out of the first portion 200 of the central bore 76 of the second bevel gear 66. Movement of the key 79 into and out of the first portion 200 of the central bore 76 moves the second bevel gear 66 into and out of engagement with the transmission shaft 68 to facilitate manual rotation of the transmission shaft 68 independent of the motor assembly 40 as described in further detail below.

Figure 12:
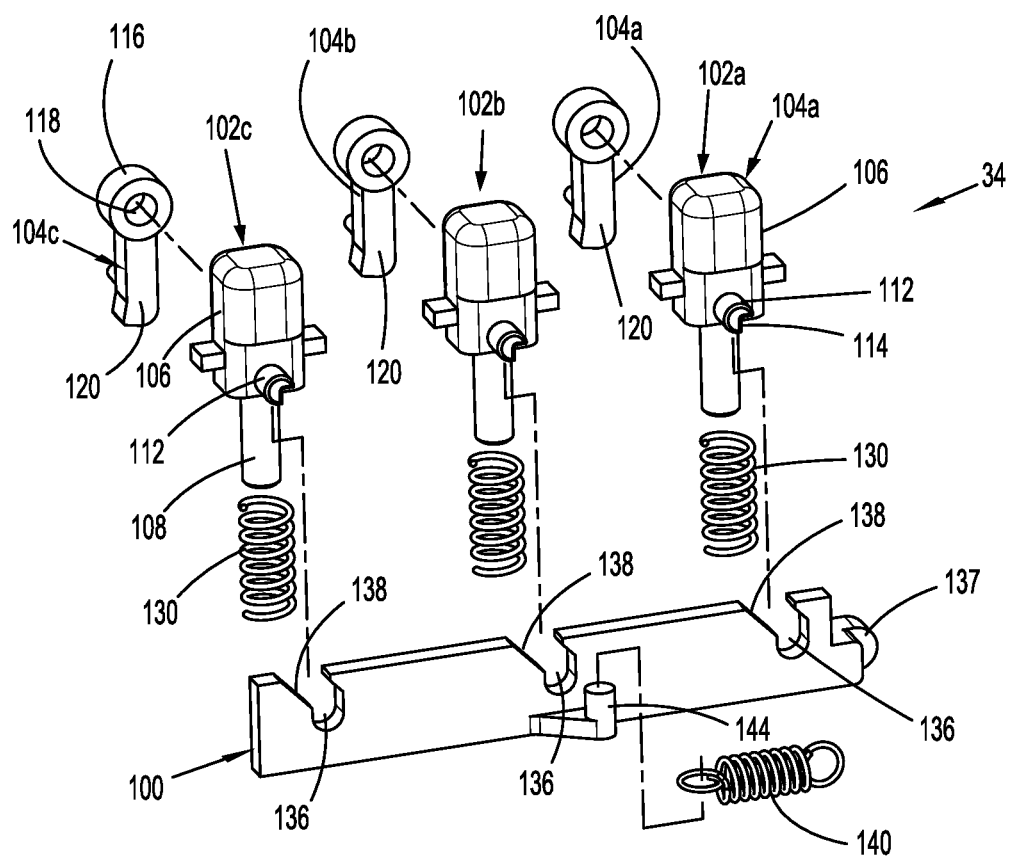
FIG. 12 is a side perspective exploded view of the staple reload select button assembly of the handle assembly shown in FIG. 5.
Figure 13:
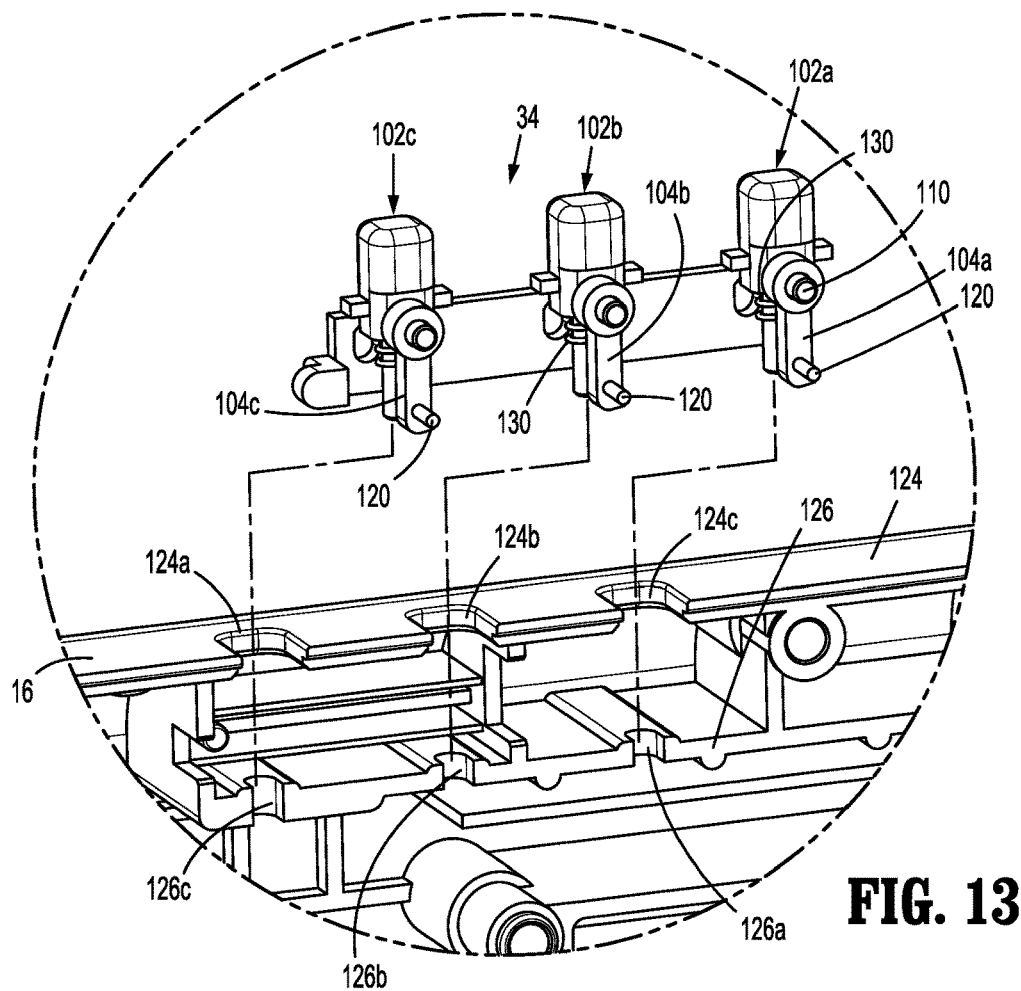
FIG. 13 is an enlarged view of the indicated area of detail shown in FIG. 5.
Figure 14:
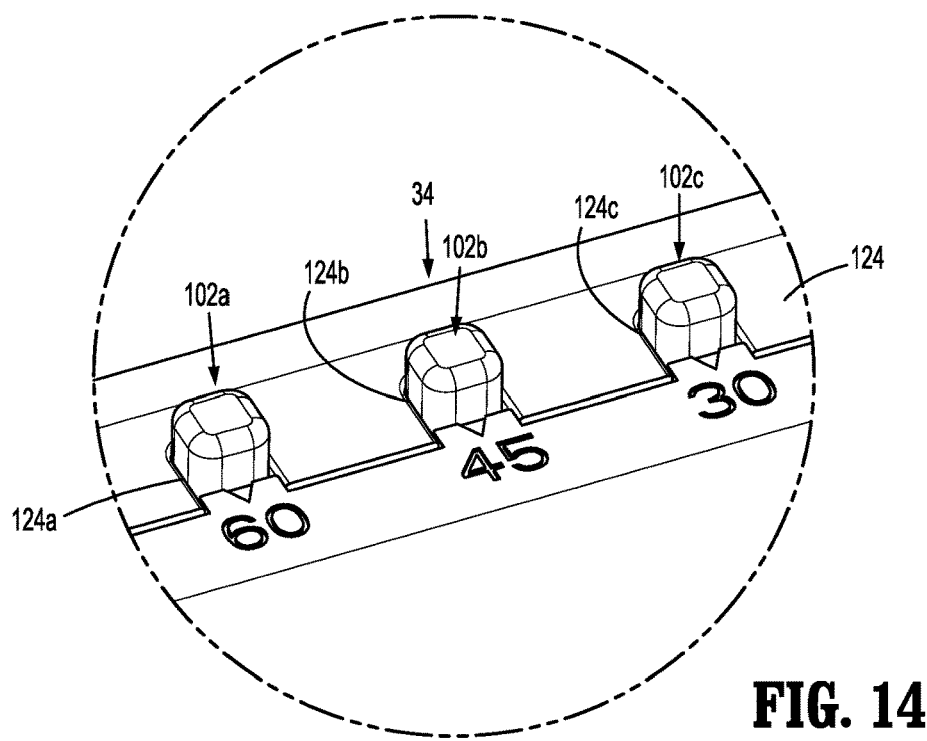
FIG. 14 is an enlarged view of the indicated area of detail shown in FIG. 3.
Figure 15:
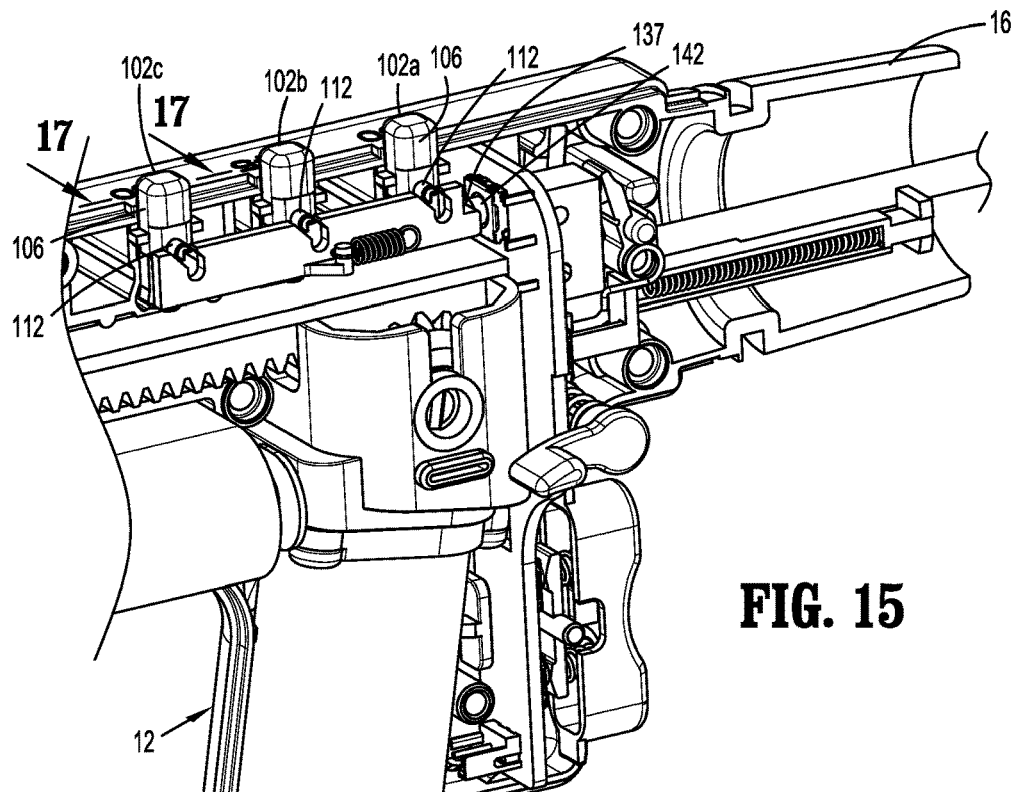
FIG. 15 is an opposite side view of the handle assembly of the stapling device shown in FIG. 1 with the other housing half-section removed.

Referring to FIGS. 12-14, the staple reload select mechanism 34 includes plurality of actuator assemblies 101a-c. Each of the actuator assemblies 101a-c includes a slide member 100, an actuator 102, and a retainer 104. Each of the actuators 102 include a body 106 and a shaft 108 that extends downwardly from the body 106 into the housing 16 (FIG. 13) of the handle assembly 12. The body 106 includes a pivot pin 110 (FIG. 13) that extends from a first side of the body 106 and a cam member 112 (FIG. 12) that extends from a second side of the body 106 opposite to the first side of the body 106. The cam member 112 includes a notch 114.

Each of the retainers 104 includes a body 116 defining a through bore 118, and a guide member 120 (FIG. 13) that extends transversely from the body 116. The through bore 118 of each of the retainers 104 a pivot pin 110 of a respective one of the actuators 102 such that each of the retainers 104 can pivot about the pivot pin 110 of the respective actuator 102.

Figure 16:
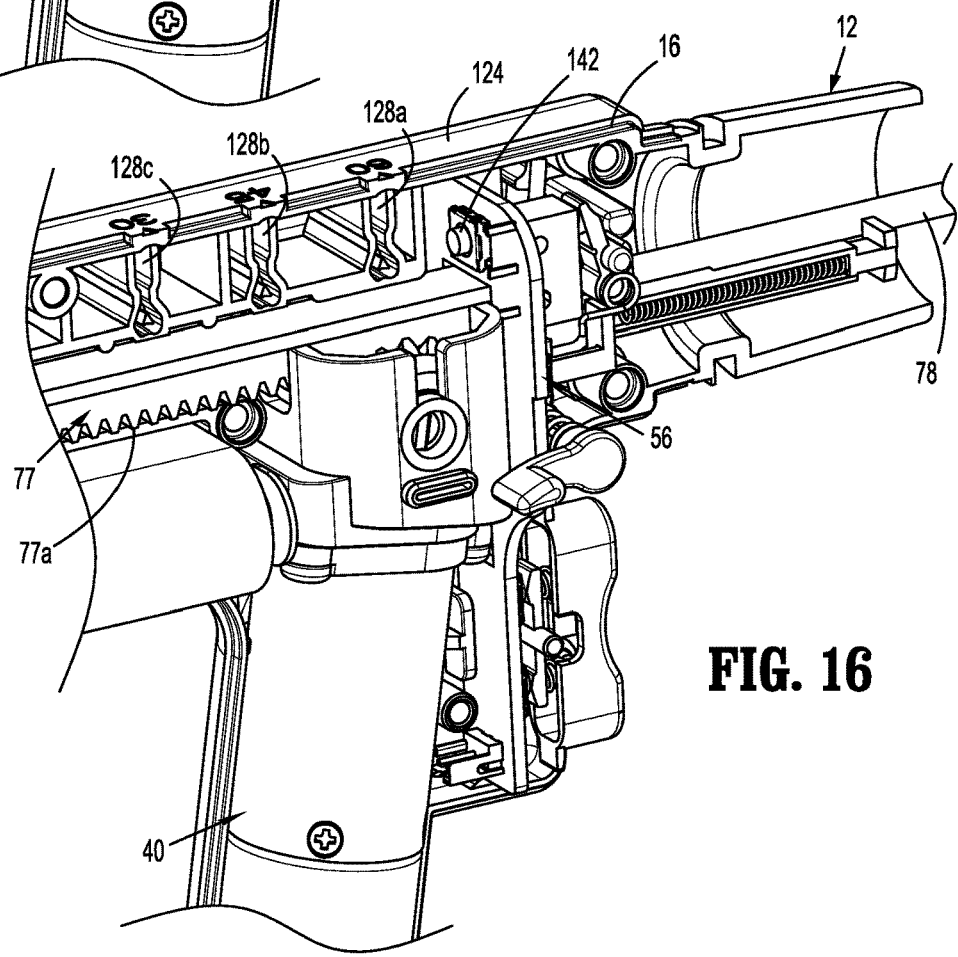
FIG. 16 is side view of the handle assembly shown in FIG. 15 with the staple reload select button assembly removed from the handle assembly.

The housing 16 of the handle assembly 12 includes an outer shell portion 124 that defines openings 124a-c and an internal shelf 126 (FIG. 13) that defines openings 126a-c. The housing 16 also defines a plurality of spaced guide slots 128a-c (FIG. 16) that are longitudinally spaced along the length of the housing 16 of the handle assembly 12. The actuators 102 extend through the openings 124a-c (FIG. 13), respectively, in the housing 16 such that the shafts 108 of the actuators 102 extend through the openings 126a-c in the internal shelf 126 of the housing 16. A biasing member, e.g., coil spring 130, is positioned in compression about the shaft 108 of each of the actuators 102 between the body 106 of the actuator 102 and the internal shelf 126 of the housing 16 to urge the actuators 102 outwardly of the cavity 50 of the housing 16 through the openings 124a-c. The retainers 104 are supported on the respective actuators 102 such that each of the guide members 120 is received in a respective one of the guide slots 128a-c (FIG. 16) defined in the housing 16 of the handle assembly 12. A portion of the pivot pins 110 of each the actuators 102 is also received in a respective one of the guide slots 128a-c (FIG. 17) of the housing 16 of the handle assembly 12.

Referring to FIGS. 12-16, the slide member 100 (FIG. 12) of the staple reload select mechanism 34 defines a plurality of cam slots 136 and includes a distal finger 137. The slide member 100 is movable from an advanced position to a retracted position. Each of the cam slots 136 is defined by an angled wall 138 that is aligned with the cam member 112 of a respective one of the actuators 102. The slide member 100 is biased distally by a spring 140 to urge the finger 137 into contact with a switch 142 (FIG. 15) that controls operation of the motor assembly 40 as discussed in further detail below. In embodiments, the spring 140 is a coil spring and the slide member 100 includes a spring mount 144 (FIG. 12) that is coupled to one end of the spring 140. The other end of the spring 140 is coupled to the housing 16 such that the slide member 100 is urged distally towards the advanced position in contact with the switch 142 (FIG. 15) to activate the switch 142. Although not described in detail herein, the switch 142, when activated, disables the motor assembly 40 to stop advancement of the drive rack 77.

Figure 17:
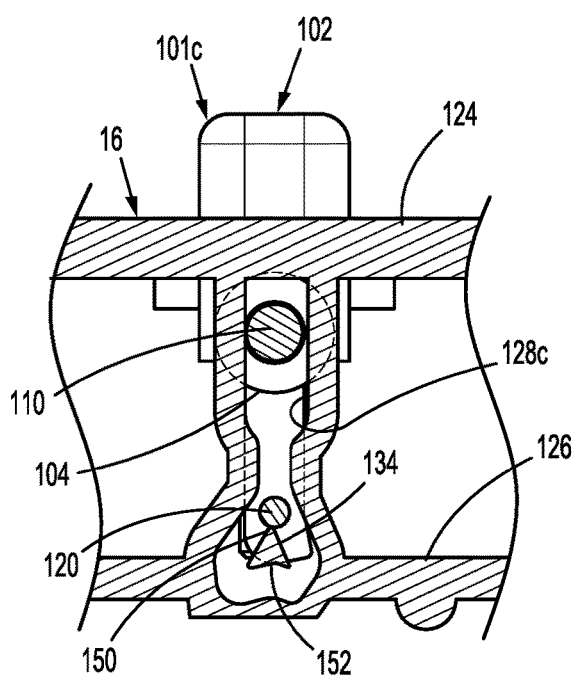
FIG. 17 is a side cross-sectional view taken along section line 17-17 of FIG. 15 showing the staple reload select button assembly in an initial non-actuated position.

Referring also to FIGS. 17-20, each of the guide slots 128a-c includes an abutment 134 that is positioned in the guide slot 128a-c at a location to engage the guide member 120 of the retainer 104. The actuators 102 are movable within the openings 124a-c and 126a-c (FIG. 13) of the housing 16 between an initial position (FIG. 17) in which the body 106 of each of the actuators 102 extends furthest outwardly from the openings 124a-c in the housing 16 to a depressed position in which the actuators 102 are pressed further into the housing 16 of the handle assembly 16 against the bias of the springs 130 (FIG. 17).

Figure 18:
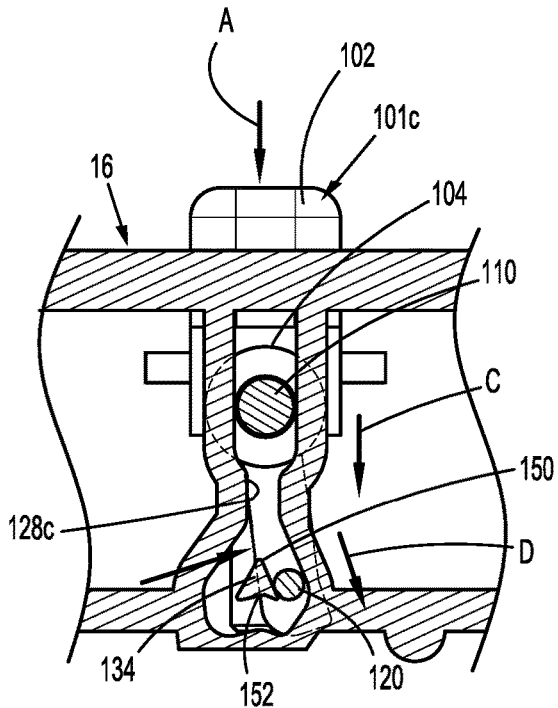
FIG. 18 is a side cross-sectional view of the portion of the handle assembly shown in FIG. 17 with the button of the staple reload select button assembly in a partially actuated position.
Figure 19:
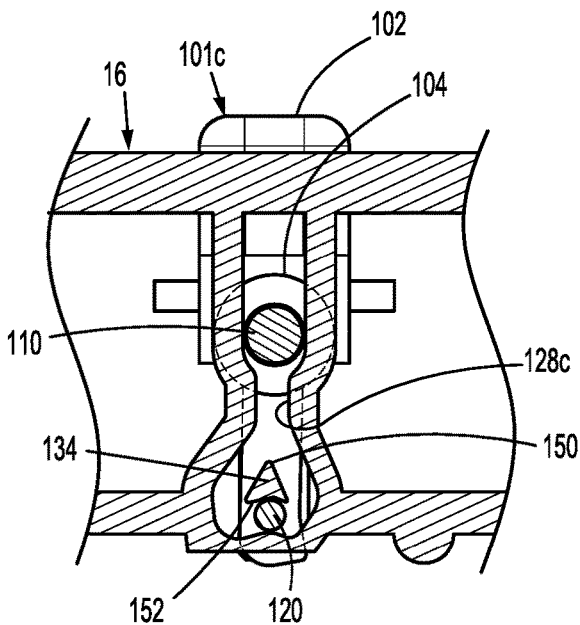
FIG. 19 is a side cross-sectional view of the portion of the handle assembly shown in FIG. 18 with the button of the staple reload select button assembly in an actuated position.

Referring to FIGS. 17-23, one of the abutments 134 is positioned in each of the guide slots 128a-c at a location to engage the guide member 120 of the retainer 104. More specifically, each of the actuators 102 is movable within a respective one of the openings 124a-c and 126a-c of the housing 16 between an initial position (FIG. 17) and an actuated position (FIG. 19.) In the initial position of each of the actuators 102, the actuator 102 extends outwardly from the respective opening 124a-c (FIG. 13) in the housing 16 and the guide member 120 of the retainer 104 associated with the actuator 102 is positioned above the respective abutment 134 as viewed in FIG. 17. In addition, the cam member 112 (FIG. 21) of the actuator 102 is positioned adjacent the angled wall 138 defining the cam slot 136 of the slide member 100 that is associated with the respective actuator 102. In this position, the finger 137 of the slide member 100 is urged by the spring 140 to the advanced position into contact with the switch 142 to activate the switch 142.

In embodiments, each of the abutments 134 has a triangular shape and includes an apex 150 and a bottom retaining wall 152 as viewed in FIGS. 17-20. The bottom retaining wall may define a concavity. When the actuator 102 is in the initial position, the guide member 120 of each of the retainers 104 is aligned with the apex 150 of a respective abutment 134. When the actuator 102 is depressed by a clinician in the direction indicated by arrows "A" in FIGS. 18 and 22, the cam member 112 (FIG. 21) of the actuator 102 engages the angled wall 138 defining the cam slot 136 in the slide member 100. Engagement between the cam member 112 and the angled wall 138 causes the slide member 100 to move proximally within the housing 16 in the direction indicated by arrows "B" in FIGS. 22 and 23 to move the finger 137 of the slide member 100 away from the switch 142 and deactivate the switch. When the switch 142 is deactivated, the motor assembly 40 will be activated upon actuation of the trigger 18.

Referring to FIGS. 18 and 19, as discussed above the retainer 104 supporting the guide member 120 is connected to the actuator 102 by the pivot pin 110. Thus, as the actuator 102 moves in the direction indicated by arrow "A" in FIG. 18, the guide member 120 is moved through the guide channel 128c in the direction indicated by arrow "C" into engagement with the apex 150 of the abutment 134. When the guide member 120 engages the apex 150 of the abutment 134, the guide member 120 is directed around the abutment 134 in the direction indicated by arrow "D" around the abutment 134 and into engagement with the retaining wall 152 of the abutment 134. Engagement of the guide member 120 of the retainer 104 with the retaining wall 142 of the abutment 134 retains the actuator 102 in the actuated position (FIG. 19) against the bias of the spring 130 (FIG. 12), to retain the slide member 100 in a position spaced from the switch 142.

Figure 23:
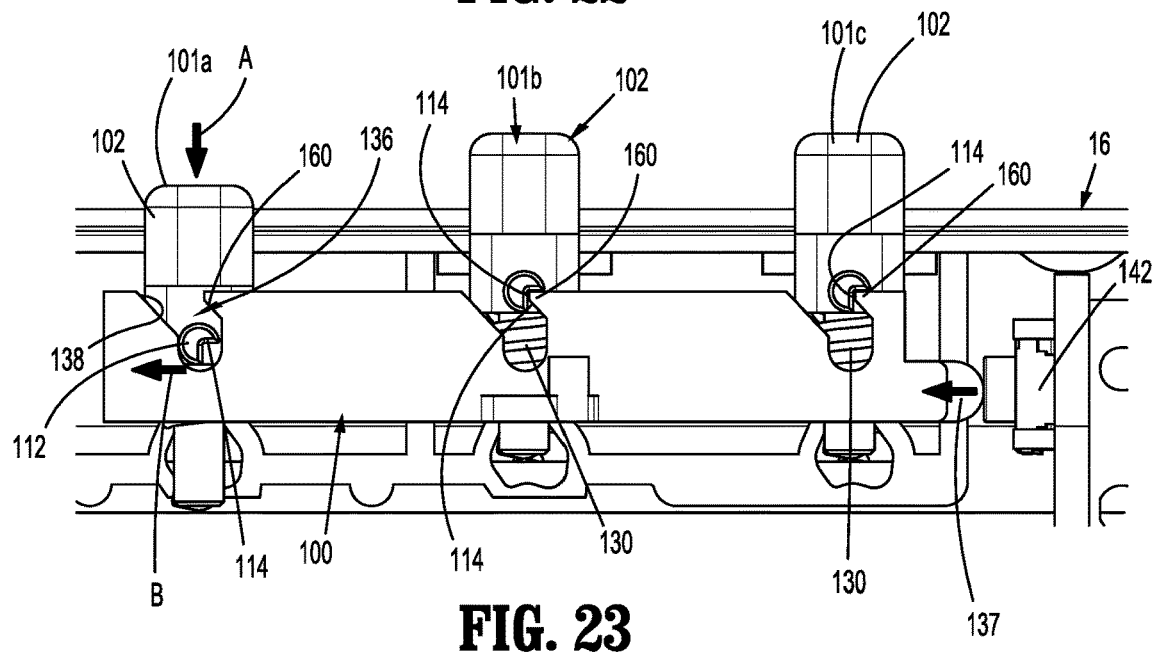
FIG. 23 is a side view of the portion of the handle assembly shown in FIG. 22 with the button of the staple reload select button assembly in its actuated position and the other two buttons of the staple reload select button assembly locked out.
Figure 24:
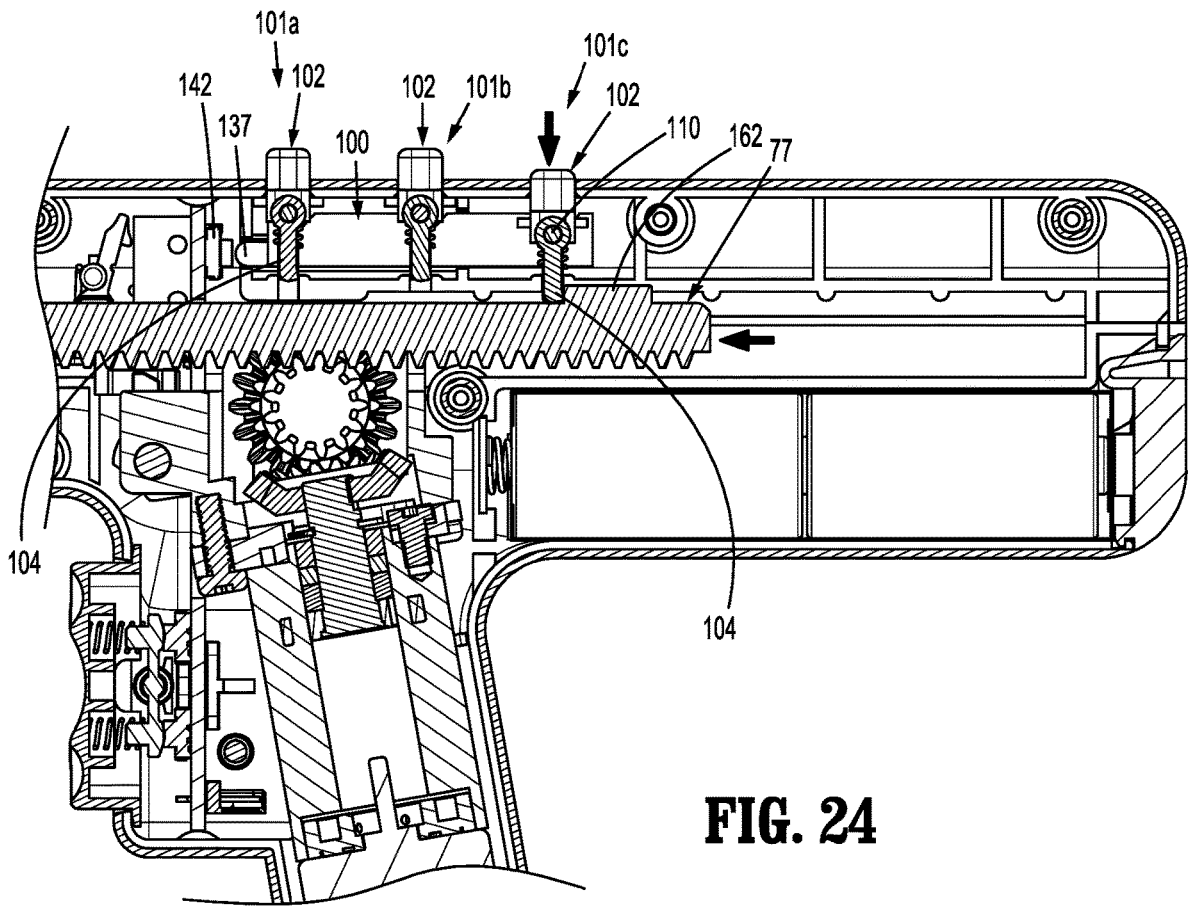
FIG. 24 is a side cross-sectional view of a proximal portion of the handle assembly shown in FIG. 13 with the 30 mm button of the staple reload select button assembly in the actuated position and the rack in its advanced position.

Referring to FIGS. 23 and 24, the slide member 100 includes a locking member 160 position adjacent to each of the cam slots 136. The locking members 160 allow only one of the actuators 102 to be depressed to the actuated position at one time. When one of the actuators 102 is depressed from its initial position to its actuated position and the slide member 100 is moved in the direction indicated by arrow "B" in FIG. 23, the locking members 160 formed on the slide member 100 move into the notches 114 formed in the cam members 112 of the actuators 102 to prevent movement of the respective actuators 102 towards their actuated positions. It is noted that although leftmost actuator 102 is shown in the actuated position and the other actuators 102 are shown locked out, movement of any one of the actuators 102 to the actuated position will move the slide member 100 to a position to lock out the two remaining actuators 102.

Figure 20:
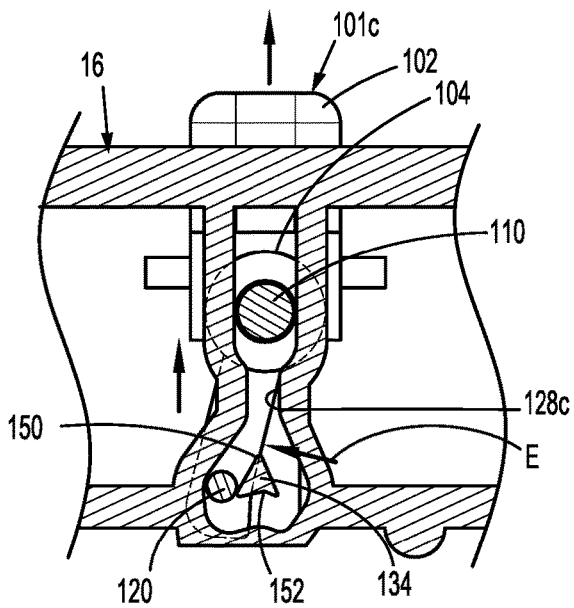
FIG. 20 is a side cross-sectional view of the portion of the handle assembly shown in FIG. 19 with the button of the staple reload select button assembly in a released position.
Figure 21:
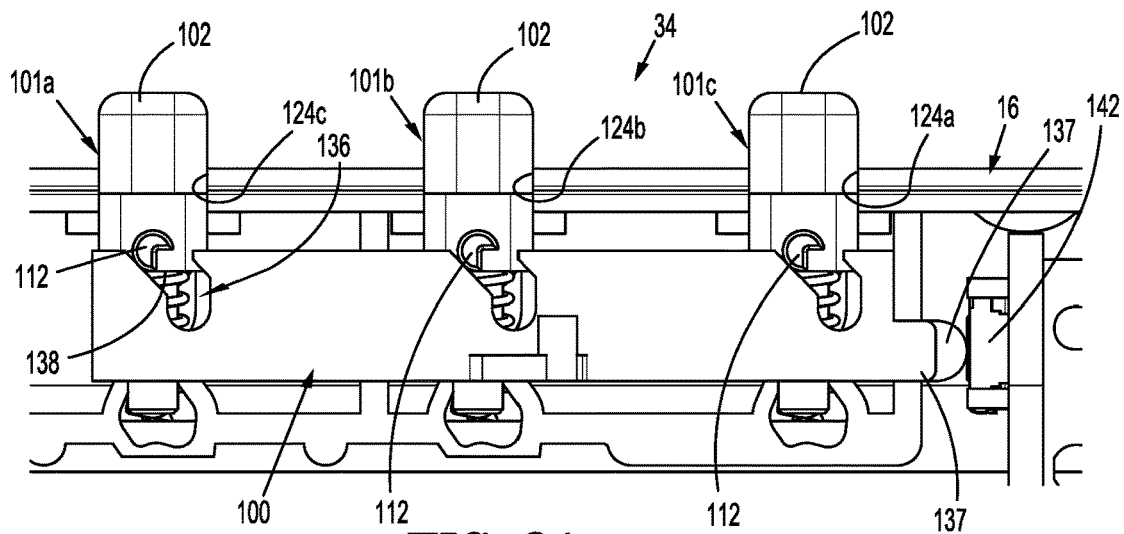
FIG. 21 is a side view of a portion of the handle assembly supporting the staple reload select button assembly with the staple reload select button assembly in its initial non-actuated position.
Figure 22:
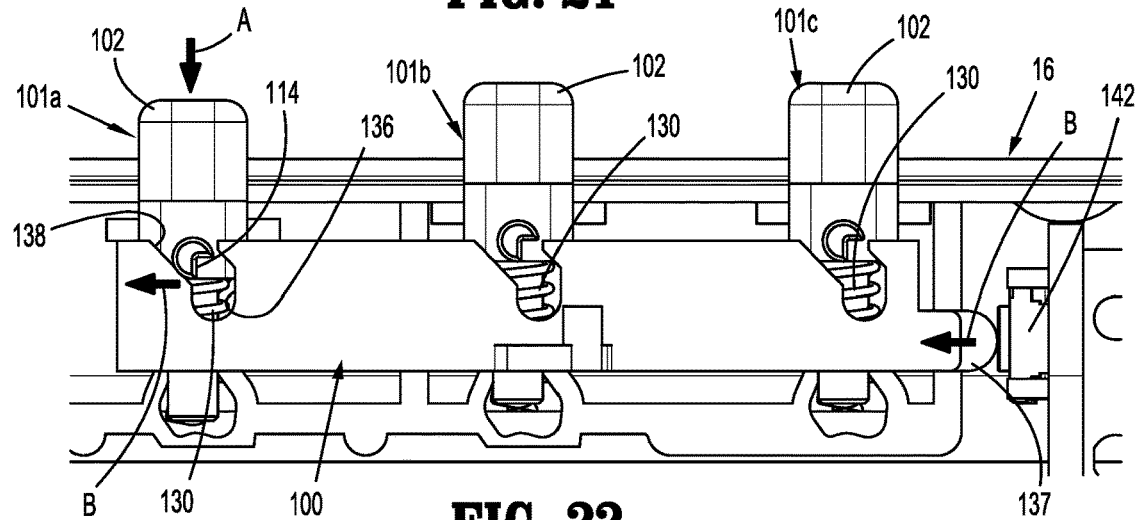
FIG. 22 is a side view of the portion of the handle assembly shown in FIG. 21 with a button of the staple reload select button assembly in its partially actuated position.

Referring to FIGS. 20 and 24, when one of the actuators 102 is moved to the actuated position, the retainer 104 associated with that actuator 102 is moved to a position aligned with an engagement surface 162 (FIG. 24) on the drive rack 77. When the drive rack 77 is advanced to fire staples from the stapling device 10, the engagement surface 162 engages the respective retainer 104 (FIG. 24) and pivots the retainer 104 in a distal direction about the pivot pin 110 to move the guide member 120 in the direction indicated by arrow "E" in FIG. 20. As the retainer 104 pivots in the direction indicated by arrow "E", the guide member 120 (FIG. 20) moves out of engagement with the retaining wall 152 of the abutment 134 to a position distally of the retaining wall 152. When this occurs, the spring 130 (FIG. 23) of the actuator assembly 101c returns the actuator 102 back to its initial position shown in FIG. 21 which allows the spring 140 (FIG. 12) to return the slide member 100 back to its advanced position also shown in FIG. 21 engaged with the switch 142 such that slide member 100 applies a load on the switch 142 to activate the switch 142. When the finger 137 of the slide member 100 activates the switch 142, the motor assembly 40 is deactivated to prevent further advancement of the drive rack 77.

As illustrated in FIG. 24, the actuators 102 and retainers 104 of the staple reload select mechanism 34 are longitudinally spaced along the housing 16 and are positioned to engage the engagement surface 162 (FIG. 24) of the drive rack 77 at different longitudinal positions along the housing 16 to control the stroke of the drive rack 77. As such, the actuator a selected one of the actuator assemblies can be depressed to selectively control the stroke of the drive rack 77. For example, the actuator 101c can be positioned on the housing 16 to provide a drive rack 77 firing stroke of 30 mm, the actuator 102b can be positioned on the housing 16 to provide a drive rack 77 firing stroke of 45 mm, and the actuator 102 can be positioned on the housing 16 to provide a drive rack firing stroke of 60 mm. Although the presently disclosed reload select mechanism 34 of the device 10 is shown to have three actuators, it is envisioned that the reload select mechanism 34 of the device 10 may include one or more actuators, e.g., 2, 3, 4, 5 or 6, which are positioned to provide a firing stroke of any length. By selectively controlling the length of the stroke of the drive rack 77, the handle assembly 12 of the stapling device 10 can be adjusted to accommodate staple reloads 14 having a variety of different staple lengths of staple rows.

Figure 29:
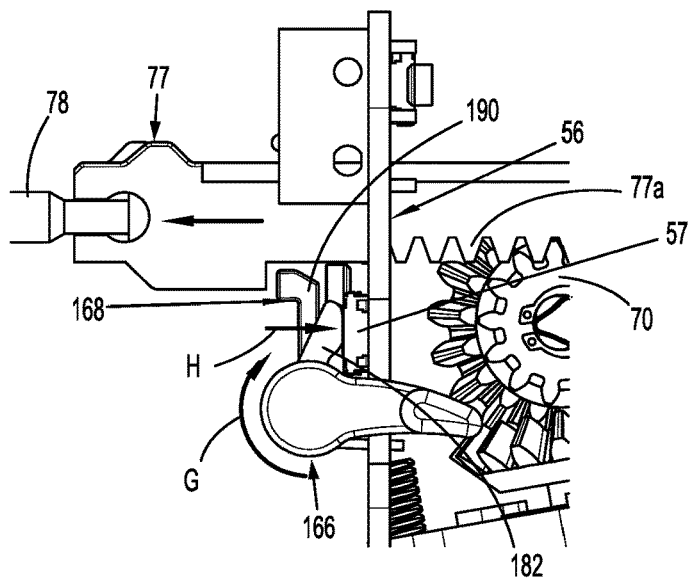
FIG. 29 is a side perspective view of the portion of the handle assembly shown in FIG. 28 with the safety toggle mechanism in a firing state.

Referring to FIGS. 25 and 26, the safety toggle assembly 36 includes a shaft 164, a toggle 166 supported on each end of the shaft 164, a retaining member 168 supported on the shaft 164, a first biasing member 170, and a second biasing member 172. The shaft 164 extends through the housing 16 and is supported for rotation such that the toggle assembly 36 is movable between a clamping state (FIG. 27) and a firing state (FIG. 29). The shaft 164 includes opposite ends that extend through opposite sides of the housing 16 and are coupled to the toggles 166 such that rotation of the toggles 166 causes rotation of the shaft 164. In embodiments, each of the toggles 166 defines a non-circular, e.g., D-shaped, bore 176 FIG. 26) that receives a non-circular, e.g., D-shaped, end 178 of the toggles 166 to rotatably secure the toggles 166 to the shaft 164. Alternately, other techniques can be used to secure the toggles 166 to the shaft 164 of the safety toggle mechanism 36.

Referring also to FIGS. 27 and 28, the shaft 164 defines a channel 180 (FIG. 26) that is positioned along on one side of the shaft 164 and includes an abutment member 182 positioned on the other side of the shaft 164. The shaft 164 extends through a bracket 184 (FIG. defined within the housing 16. The channel 180 is positioned on one side of the bracket 184 and the abutment member 182 is positioned on an opposite side of the bracket 184. The first biasing member 170, which may be a torsion spring, is positioned between the abutment 182 and the bracket 184 of the housing 16 to rotatably bias the shaft 164 towards a non-firing state. The bracket 184 supports the PCB 56 which supports the switch 57. In the non-firing state (FIG. 27), the abutment member 182 is spaced from the switch 57. In the firing state, the abutment member 182 applies a load on the switch 57 to actuate the switch 57. When the switch 57 is activated, the motor assembly 40 can be actuated with the trigger 18 to fire the stapling device 10.

The retaining member 168 includes a hub 188 that defines a bore 188a (FIG. 26) and an arm 190. The bore 188a receives the shaft 164. The hub 188 includes a tab 192 that extends into the bore 188a and is received within the channel 180 of the shaft 164 to rotatably secure the retaining member 168 to the shaft 164 but allow the retaining member 168 to move along the shaft 164 over the length of the channel 180. The second biasing member 172 is positioned between one of the toggles 166 and the hub 188 of the retaining member 168 to urge the retaining member 168 along the hub 188 towards the bracket 184.

The bracket 184 supports a stop 196 (FIG. 30) that is fixedly positioned within the housing 16. The stop 196 includes a tapered distal surface 196a and a proximal stop surface 198. When the safety toggle assembly 36 is in the non-firing state (FIG. 28), the arm of the retaining member 168 is positioned on a distal side of the stop 196.

Figure 30:
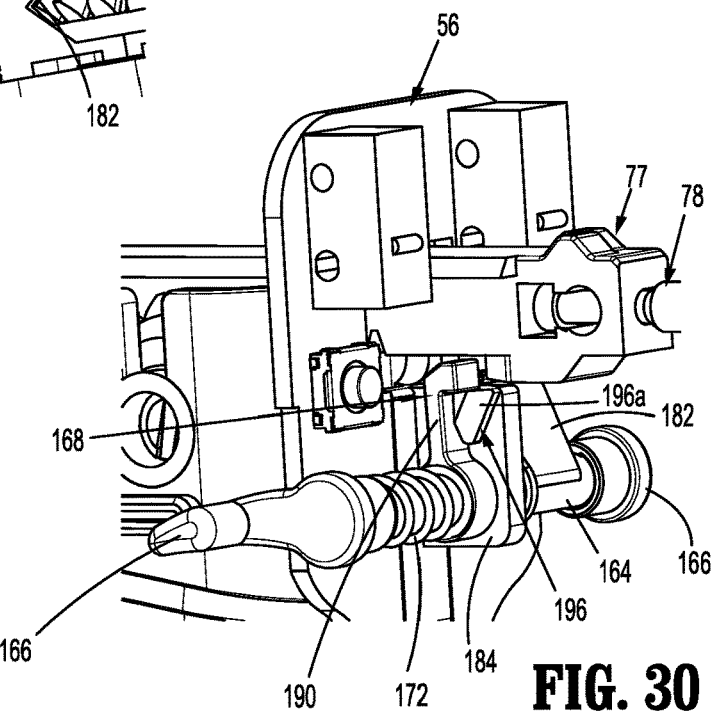
FIG. 30 is a side perspective view from the distal end of the portion of the handle assembly shown in FIG. 29 with the safety toggle mechanism in the firing state.
Figure 31:
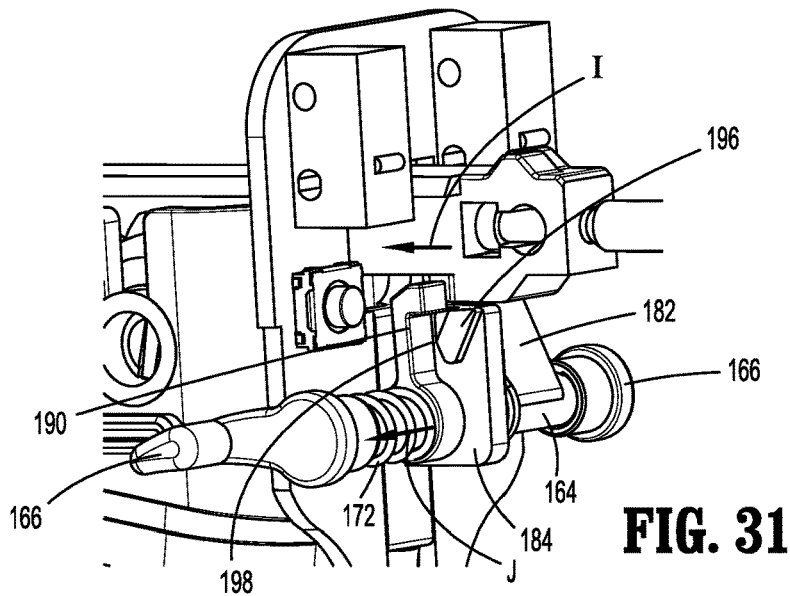
FIG. 31 is a side perspective view from the distal end of the portion of the handle assembly shown in FIG. 30 as the safety toggle mechanism is reset to the clamping state.

Referring to FIGS. 29-31, when the safety toggle assembly 36 is rotated from the non-firing state to the firing state in the direction indicated by arrow "G" in FIG. 29, the shaft 164 rotates to move the abutment member 182 in the direction indicated by arrow "H" into the switch 57 to apply a load to the switch 57 to move the safety toggle assembly 36 from the non-firing state (FIG. 28) to the firing state (FIG. 29). As the shaft 164 rotates in the direction indicated by arrow "G" in FIG. 29, the arm 190 of the retaining member 168 engages and moves over the stop 196 (FIG. 30) on the bracket 184 in the direction indicated by arrow "I" in FIG. 31 to a position adjacent the proximal stop surface 198 (FIG. 31) of the stop 196 to retain the safety toggle assembly 36 in the firing state. As the arm 190 passes over the stop 196, the retaining member 168 is pushed outwardly against the bias of the second biasing member 172 in the direction indicated by arrow "J" in FIG. 31 such that the second biasing member 172 compresses and the tab 192 slides within the channel 180 (FIG. 26) of the shaft 164. When the arm 190 passes over the stop 196, the second biasing member 172 snaps the retaining member 168 in place behind the stop 196 of the bracket 184. As discussed above, the stop 196 and retaining member 168 cooperate to retain the abutment member 182 in contact with the switch 57 to allow the safety toggle assembly 36 to remain in the firing state without holding onto the toggles 166.

Referring to FIGS. 32-35, in cases of emergency, it may be necessary to manually retract the drive rack 77. As discussed above, the transmission shaft 68 supports a key 79 that is received in the central bore 76 of the second bevel gear 66. In embodiments, the central bore 76 of the second bevel gear 66 includes a first portion 200 that has a shape that corresponds to the shape of the key 79 and a second portion 202 that is configured to permit rotation of the key 79 independently of the second bevel gear 66. The spring 96 is positioned between the pinion 70 and the second bevel gear 66 to urge the transmission shaft 68 to a position in which the key 79 is positioned within the first portion 200 of the central bore 76 of the second bevel gear 66 such that rotation of the second bevel gear 66 causes rotation of the transmission shaft 68 which causes longitudinal movement of the drive rack 77.

Referring to FIGS. 33-35, in embodiments, the housing 16 defines an access opening 204 that provides access to the engagement end 98 of the transmission shaft 68. A removable cover 204 may be provided to close the opening 206. If an emergency arises and the motor assembly 40 is not functioning, the cover 206 can be removed from within the access opening 206 to access the engagement end 98 of the transmission shaft 68. Next, a tool (not shown) may be provided that is configured to be coupled to the engagement end 98 of the of the transmission shaft 68. The transmission shaft 68 can be pressed inwardly in the direction indicated by arrow "K" in FIG. 35 to move the key 79 on the transmission shaft 68 from the first portion 200 of the central bore 76 of the second bevel gear 66 into the second portion 202 of the central bore 76 of the second bevel gear 66. With the key 79 positioned in the second portion 202 of the central bore of the second bevel gear 66, the transmission shaft 68 can be rotated independently of the second bevel gear 66 in the directions indicated by arrows "L" to rotate the pinion 70. As discussed above, the pinion 70 is coupled to the drive rack 77. As such, rotation of the pinion 70 causes longitudinal translation of the drive rack 77.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical device comprising:
   a device housing;
   a motor assembly supported within the device housing;
   a drive member supported within the device housing and movable between an advanced position and a retracted position;
   a tool assembly; and
   a gear assembly positioned within the device housing between the motor assembly and the drive member, the gear assembly including a first gear engaged with the motor assembly, a transmission shaft, a second gear engaged with the first gear and supported on the transmission shaft, and a pinion fixedly supported on the transmission shaft and engaged with the drive member, the transmission shaft movable in relation to the second gear from a first position in which the transmission shaft is rotatably fixed to the second gear and a second position in which the transmission shaft is rotatable independently of the second gear;
   wherein in the first position of the transmission shaft, rotation of the first gear causes rotation of the second gear to rotate the pinion to cause movement of the drive member, and in the second position of the transmission shaft, the transmission shaft is rotatable independently of the second gear such that the transmission shaft can be manually rotated to move the drive member within the device housing independently of the motor assembly.

2. The surgical device of claim 1, wherein the gear assembly includes a biasing member, the biasing member being positioned to urge the transmission shaft to the second position.

3. The surgical device of claim 2, wherein the biasing member is positioned between the pinion and the second gear.

4. The surgical device of claim 3, wherein the biasing member includes a coil spring.

5. The surgical device of claim 1, wherein the transmission shaft includes an engagement end, and the device housing defines an access opening that is positioned and configured to provide access to the engagement end of the transmission shaft to facilitate movement of the transmission shaft between the first and second positions.

6. The surgical device of claim 5, wherein the engagement end of the transmission shaft is configured to engage a retraction tool to facilitate manual rotation of the transmission shaft.

7. The surgical device of claim 6, wherein the engagement end of the transmission shaft has a non-circular configuration.

8. The surgical device of claim 5, further including a cover that is received within the access opening to close the access opening, the cover removable from the access opening to provide access to the transmission shaft.

9. The surgical device of claim 1, wherein the transmission shaft includes a key and the second gear defines a central bore, the central bore having a first portion that has a shape that corresponds to the key and a second portion that is configured to permit rotation of the key within the central bore, the key positioned within the first portion of the central bore in the first position of the transmission shaft and the key positioned in the second portion of the central bore when the transmission shaft is in the second position.

10. The surgical device of claim 1, wherein the gear assembly includes a gear housing, the gear housing having a first side defining a bore and a second opposite side defining a circular cutout, the transmission shaft having a first end extending through the bore in the first side of the gear housing and a second end supported by the second gear, the second gear including a hub that is rotatably supported within the circular cutout in the second opposite side of the gear housing such that the transmission shaft, the second gear, and the pinion are rotatably supported within the gear housing.

11. The surgical device of claim 10, wherein the gear housing includes outwardly extending protrusions and the device housing defines slots, wherein the slots are configured to receive the protrusions to locate and secure the gear housing within the device housing.

12. The surgical device of claim 10, wherein the motor assembly includes a motor and a gearbox.

13. The surgical device of claim 12, wherein the gear housing is secured to the gearbox of the motor assembly with a mounting plate.

14. The surgical device of claim 1, further including a control rod having a proximal end coupled to the drive member and a distal end coupled to the tool assembly, wherein longitudinal movement of the drive member causes corresponding longitudinal movement of the control rod.

15. A powered assembly comprising:
   a first housing;
   a motor assembly supported within the first housing;

a drive member supported within the first housing, the drive member being movable within the first housing between an advanced position and a retracted position; and a gear assembly supported within the first housing between the motor assembly and the drive, the gear assembly including a first gear engaged with the motor assembly, a transmission shaft, a second gear engaged with the first gear and supported on the transmission shaft, and a pinion fixedly supported on the transmission shaft and engaged with the drive member, the transmission shaft being movable in relation to the second gear from a first position in which the transmission shaft is rotatably fixed to the second gear and a second position in which the transmission shaft is rotatable independently of the second gear, wherein in the first position of the transmission shaft, rotation of the first gear causes rotation of the second gear to rotate the pinion to cause longitudinal movement of the drive member, and in the second position of the transmission shaft, the transmission shaft is rotatable independently of the second gear such that the transmission shaft can be manually rotated to move the drive member longitudinally within the first housing independently of the motor assembly.

16. The powered assembly of claim 15, wherein the gear assembly includes a biasing member positioned between the second gear and the pinion, the biasing member being positioned to urge the transmission shaft to the second position.

17. The powered assembly of claim 15, wherein the transmission shaft includes an engagement end, and the first housing defines an access opening that is positioned and configured to provide access to the engagement end of the transmission shaft to facilitate movement of the transmission shaft between the first and second positions.

18. The powered assembly of claim 15, wherein the transmission shaft includes a key and the second gear defines a central bore, the central bore having a first portion that has a shape that corresponds to the key and a second portion that is configured to permit rotation of the key, the key being positioned within the first portion of the central bore in the first position of the transmission shaft and the key being positioned in the second portion of the central bore when the transmission shaft is in the second position.

19. The powered assembly of claim 15, wherein the gear assembly includes a gear housing, the gear housing having a first side defining a bore and a second opposite side defining a circular cutout, the transmission shaft having a first end extending through the bore in the first side of the gear housing and a second end supported by the second gear, the second gear including a hub that is rotatably supported within the circular cutout in the second opposite side of the gear housing such that the transmission shaft, the second gear, and the pinion are rotatably supported within the gear housing.

20. The powered assembly of claim 19, wherein the gear housing includes outwardly extending protrusions and the first housing defines slots, wherein the slots are configured to receive the protrusions to locate and secure the gear housing within the first housing.

* * * * *